(12) United States Patent
Harman et al.

(10) Patent No.: US 11,017,655 B2
(45) Date of Patent: May 25, 2021

(54) HAND SANITATION COMPLIANCE ENFORCEMENT SYSTEMS AND METHODS

(71) Applicant: VISUALQ, Pepper Pike, OH (US)

(72) Inventors: John Caleb Harman, Downers Grove, IL (US); John M. Abdelsayed, Pepper Pike, OH (US)

(73) Assignee: VISUALQ, Pepper Pike, OH (US)

( * ) Notice: Subject to any disclaimer, the term of this patent is extended or adjusted under 35 U.S.C. 154(b) by 0 days.

(21) Appl. No.: 17/067,172

(22) Filed: Oct. 9, 2020

(65) Prior Publication Data

US 2021/0110700 A1 Apr. 15, 2021

Related U.S. Application Data

(60) Provisional application No. 62/912,787, filed on Oct. 9, 2019.

(51) Int. Cl.
  *G08B 21/24* (2006.01)
  *G06K 9/00* (2006.01)
  *G06K 9/62* (2006.01)
  *H04N 7/18* (2006.01)
  *G08B 5/36* (2006.01)
  (Continued)

(52) U.S. Cl.
  CPC ....... *G08B 21/245* (2013.01); *G06K 7/10297* (2013.01); *G06K 7/10415* (2013.01); *G06K 9/00744* (2013.01); *G06K 9/6256* (2013.01); *G06N 20/00* (2019.01); *G06Q 10/10* (2013.01); *G06Q 30/018* (2013.01); *G06Q 30/0261* (2013.01); *G08B 5/36* (2013.01);

*G16H 15/00* (2018.01); *G16H 40/20* (2018.01); *H04N 7/183* (2013.01)

(58) Field of Classification Search
  CPC ........ G08B 21/245; G08B 5/36; G16H 40/20; G16H 15/00; G06N 20/00; G06K 7/10297; G06K 7/10415; G06K 9/00744; G06K 9/6256; G06Q 10/10; G06Q 30/018; G06Q 30/0261; H04N 7/183
  See application file for complete search history.

(56) References Cited

U.S. PATENT DOCUMENTS 6,038,331 A * 3/2000 Johnson ............. G06K 9/00375
  134/113
10,002,518 B1 * 6/2018 Wheeler ............. G08B 21/245
  (Continued)

*Primary Examiner* — Joseph H Feild
*Assistant Examiner* — Rufus C Point
(74) *Attorney, Agent, or Firm* — Marshall, Gerstein & Borun LLP

(57) ABSTRACT

An electronic processor is operatively connected with at least one video camera, or additionally or alternatively a non-camera-based sensor, and at least one annunciator to process real time video acquired by the at least one video camera in real time to perform a hand hygiene compliance enforcement method for encouraging use of a hand sanitation station. The real time video is analyzed to determine an occupancy time interval over which a sanitation zone imaged by the real time video is occupied. Whether a hand sanitation event occurs is determined based on images of a wash station zone extracted from the real time video acquired during the occupancy time interval. The at least one annunciator is controlled to annunciate a hand hygiene compliance status based on the determination of whether a hand sanitation event occurs.

29 Claims, 4 Drawing Sheets

(51) Int. Cl.
*G16H 40/20* (2018.01)
*G06N 20/00* (2019.01)
*G06K 7/10* (2006.01)
*G06Q 30/00* (2012.01)
*G06Q 10/10* (2012.01)
*G16H 15/00* (2018.01)
*G06Q 30/02* (2012.01)

(56) References Cited

U.S. PATENT DOCUMENTS

| | | | | |
|---|---|---|---|---|
| 2008/0019490 A1* | 1/2008 | Lynn | .................. | G07F 9/02 379/93.01 |
| 2008/0107341 A1* | 5/2008 | Lu | .................. | G06K 9/00248 382/190 |
| 2009/0051545 A1* | 2/2009 | Koblasz | .................. | G08B 21/245 340/573.1 |
| 2009/0087028 A1* | 4/2009 | Lacey | .................. | G08B 21/245 382/103 |
| 2010/0117836 A1* | 5/2010 | Seyed Momen | .................. | G01S 1/7034 340/573.1 |
| 2012/0212582 A1* | 8/2012 | Deutsch | .................. | G16H 40/20 348/46 |
| 2013/0278635 A1* | 10/2013 | Maggiore | .................. | G06F 3/0304 345/633 |
| 2016/0042635 A1* | 2/2016 | Rosebraugh | .................. | G16H 40/20 340/573.1 |
| 2016/0048726 A1* | 2/2016 | Tang | .................. | G06K 9/00355 382/103 |
| 2016/0314683 A1* | 10/2016 | Felch | .................. | G08B 21/245 |
| 2018/0047277 A1* | 2/2018 | Thyroff | .................. | G08B 21/24 |
| 2018/0232602 A1* | 8/2018 | Dey | .................. | G06F 16/5854 |
| 2018/0301014 A1* | 10/2018 | Worral | .................. | G06K 9/00355 |
| 2018/0357886 A1* | 12/2018 | Tavori | .................. | G06F 1/163 |
| 2019/0095764 A1* | 3/2019 | Li | .................. | G06N 20/20 |
| 2020/0167715 A1* | 5/2020 | Bhatt | .................. | G06Q 10/0633 |
| 2020/0323397 A1* | 10/2020 | Simonovsky | .................. | A47K 1/04 |

* cited by examiner

HAND SANITATION COMPLIANCE ENFORCEMENT SYSTEMS AND METHODS

CROSS REFERENCE TO RELATED APPLICATION(S)

This application claims the benefit of U.S. Provisional Application No. 62/912,787 (filed on Oct. 9, 2019). The entirety of the foregoing provisional application is incorporated by reference herein.

FIELD OF THE DISCLOSURE

The present disclosure generally relates to hand sanitation compliance enforcement systems and methods, and, more particularly, to hand sanitation and/or hygiene compliance enforcement systems, devices, and/or methods relating to the hand sanitation arts and to related arts such as medical sanitation arts, culinary sanitation arts, and the like.

BACKGROUND

Hand sanitation is a critical component in areas such as healthcare, food preparation/handling, child care, restaurants, elderly care, or the like. For example, a hospital ward housing critically ill patients may have a hand sanitation station located outside the entrance door, including a wash basin, sanitizing soap, and/or the like. Doctors, nurses, or other medical personnel are expected to follow a hand hygiene protocol which includes sanitizing their hands at the hand sanitation station prior to entering the hospital ward. In some protocols, gloves may be donned after performing hand sanitation, for example in accordance with a "gown and glove" procedure such as is employed in a clostridium difficule (C-DIFF) protocol. A second hand sanitation station may be located inside the hospital ward proximate to the exit door, and the hand hygiene protocol further calls for medical personnel to sanitize their hands at the second hand sanitation station prior to exiting the hospital ward. Following the prescribed hand hygiene protocol can prevent contact-mediated spread of infectious diseases (e.g., coronavirus disease 2019 aka "COVID-19") to and/or from critically ill patients. Similar hand hygiene protocols may be established for restaurant workers or others employed in the food preparation/handling industries, for teachers who come into frequent contact with children, for workers at assisted care facilities who come into frequent contact with elderly residents, or so forth.

Unfortunately, compliance with a hand hygiene protocol is imperfect. This can lead to unnecessary spread of infectious diseases (e.g., COVID-19). Noncompliance has been addressed by educational/training programs, and by use of prominent signage to remind personnel to use the hand sanitation station. Education or training, while helpful, does not effectively prevent noncompliance due to forgetfulness or simple laziness. Prominent signage may reduce forgetfulness, but signage can easily become overfamiliar if overused. For example, a hospital may have reminder signs posted at the entrance to every patient ward; over time, hospital personnel come to tune out these ubiquitous signs thereby reducing their effectiveness. Furthermore, prominent signage is not a deterrent to noncompliance due to laziness.

For the foregoing reasons, certain improvements are disclosed herein, as there is a need for systems, devices, and methods for hand hygiene compliance and enforcement.

BRIEF SUMMARY

In accordance with some illustrative embodiments disclosed herein, a hand hygiene compliance enforcement device comprises at least one video camera, at least one annunciator, an electronic processor; and a non-transitory storage medium that stores instructions that are readable and executable by the electronic processor to process real time video acquired by the at least one video camera in real time. The instructions include occupancy detection instructions readable and executable by the electronic processor to analyze the real time video to determine an occupancy time interval over which a sanitation zone imaged by the real time video is occupied. The instructions further include sanitation detection instructions readable and executable by the electronic processor to determine whether a hand sanitation event occurs based on images of a wash station zone extracted from the real time video acquired during the occupancy time period and to control the at least one annunciator to annunciate a hand hygiene compliance status based on the determination of whether a hand sanitation event occurs.

In accordance with some illustrative embodiments disclosed herein, a hand sanitation station includes a hand sanitation station including at least a sanitation fluid dispenser, and a hand hygiene compliance enforcement device as set forth in the immediately preceding paragraph, in which the at least one video camera is arranged such that at least a portion of the hand sanitation station coincides with the wash station zone in the real time video acquired by the at least one video camera.

In accordance with some illustrative embodiments disclosed herein, a non-transitory storage medium stores instructions that are readable and executable by an electronic processor operatively connected with at least one video camera and at least one annunciator to process real time video acquired by the at least one video camera in real time to perform a hand hygiene compliance enforcement method comprising: analyzing the real time video to determine an occupancy time interval over which a sanitation zone imaged by the real time video is occupied; determining whether a hand sanitation event occurs based on images of a wash station zone extracted from the real time video acquired during the occupancy time period; and controlling the at least one annunciator to annunciate a hand hygiene compliance status based on the determination of whether a hand sanitation event occurs.

In accordance with some illustrative embodiments disclosed herein, a hand hygiene compliance enforcement method comprise: using at least one video camera, acquiring real time video of a field of view that includes a sanitation station having a wash station zone; using an electronic processor, determining whether a hand sanitation event occurs based on images of the wash station zone extracted from the real time video; and using an annunciator, annunciating a hand hygiene compliance status based on the determination of whether a hand sanitation event occurs.

As described herein, a hand hygiene compliance enforcement device is disclosed that comprises: at least one video camera; at least one annunciator; an electronic processor; and a non-transitory storage medium storing instructions that are readable and executable by the electronic processor, wherein the instructions, when executed by the electronic processor, cause the electronic processor to: process real time video acquired by the at least one video camera in real time, analyze, by execution of occupancy detection instructions, the real time video to determine an occupancy time interval over which a sanitation zone imaged by the real time video is occupied, determine, by execution of sanitation detection instructions, whether a hand sanitation event occurs based on images of a wash station zone as extracted from the real time video acquired during the occupancy time interval, and control the at least one annunciator to annunciate a hand hygiene compliance status based on the determination of whether a hand sanitation event occurs.

In additional embodiments, as described herein, a non-transitory storage medium is disclosed for storing instructions for performing a hand hygiene compliance enforcement, the instructions being readable and executable by an electronic processor, wherein the instructions, when executed by the electronic processor, cause the electronic processor to: receive real time video acquired by at least one video camera in real time; analyze the real time video to determine an occupancy time interval over which a sanitation zone imaged by the real time video is occupied; determine whether a hand sanitation event occurs based on images of a wash station zone as extracted from the real time video acquired during the occupancy time interval; and control at least one annunciator to annunciate a hand hygiene compliance status based on the determination of whether a hand sanitation event occurs.

In still further embodiments, as described herein, a hand hygiene compliance enforcement method is disclosed that comprises: acquiring, via a at least one video camera, real time video of a field of view that includes a sanitation station having a wash station zone; determining, via an electronic processor, whether a hand sanitation event occurs based on images of the wash station zone as extracted from the real time video; and annunciating, via an annunciator, a compliance status based on the determination of whether a hand sanitation event occurs.

In additional embodiments, as described herein, a hand hygiene compliance enforcement device is disclosed that comprises: at least one non-camera-based sensor; at least one annunciator; an electronic processor; and a non-transitory storage medium storing instructions that are readable and executable by the electronic processor, wherein the instructions, when executed by the electronic processor, cause the electronic processor to: process real time data output of the non-camera-based sensor in real time, analyze, by execution of occupancy detection instructions, the data output to determine an occupancy time interval over which a sanitation zone determined by the data output is occupied, determine, by execution of sanitation detection instructions, whether a hand sanitation event occurs based on the data output corresponding to a wash station zone, the data output acquired during the occupancy time interval, and control the at least one annunciator to annunciate a hand hygiene compliance status based on the hand sanitation event.

As described herein, the embodiments of the disclosure may comprise one or more video cameras and/or, additionally or alternatively, one or more non-camera based sensors. For example, while the disclosure herein refers, in many embodiments, to use of a video camera, it is to be understood that, additionally or alternatively, other motion or video-like devices could be used as a substitute for a video camera. For example, for embodiments using video camera(s), one or more images or image frames (e.g., comprising a video) as captured by the video camera(s) may turned into, or used to create, arrays of digits that represent the image. Additionally, or alternatively, for embodiments using non-camera based sensor(s) the same (or similar) array structure(s) (as created for video camera embodiments) can be emulated by non-camera based sensor(s). Such non-camera based sensor(s) can comprise, by way of non-limiting example, microwave sensor(s), depth sensor(s), tomographic sensor(s), and/or infrared (passive and active) sensor(s), or other such similar or related sensors or technologies. These non-camera based sensor(s) can provide stream(s) of data, or otherwise inputs that emulate the use of a video camera. Just as video camera input, such non-camera based sensor(s) inputs or streams of data can also serve as the base for artificial intelligence based model(s) (e.g., machine learning model(s) and/or CNN model(s)), and related model pattern recognition, as described herein. In this way, non-camera-based sensors can create (or emulate) the same (or similar) array data structure(s) that can then be used to generate tensors for pattern recognition, just as for video camera related embodiments.

In accordance with the above, and with the disclosure herein, present disclosure includes improvements in computer functionality or in improvements to other technologies at least because the claims recite that, e.g., a hand hygiene compliance enforcement device is improved by implementation of machine learning to improve the prediction accuracy of the hand hygiene compliance enforcement device to detect hand sanitation event(s) in real time. That is, the present disclosure describes improvements in the functioning of the computer itself or "any other technology or technical field" because a hygiene compliance enforcement device is better able to predict or detect hand sanitation event(s). This improves over the prior art at least because either no such device(s) existed or were limited to non-machine learning based approaches.

The present disclosure includes applying certain of the features described herein with, or by use of, a particular machine, e.g., a video camera and/or a non-camera based sensor for processing real time video or sensor data acquired by a video camera or non-camera based sensor in real time.

The present disclosure includes effecting a transformation or reduction of a particular article to a different state or thing, e.g., transforming or reducing video images and/or sensor data to actual image or audible output to indicate whether or not a hand sanitation event occurs.

The present disclosure includes specific features other than what is well-understood, routine, conventional activity in the field, or adding unconventional steps that confine the claim to a particular useful application, e.g., hand hygiene compliance enforcement devices and methods, as described herein.

Advantages will become more apparent to those of ordinary skill in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the system(s), devise(s), and method(s) disclosed therein. It should be understood that each Figure depicts an embodiment of a particular aspect of the disclosed system and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and instrumentalities shown, wherein.

Figure 1:
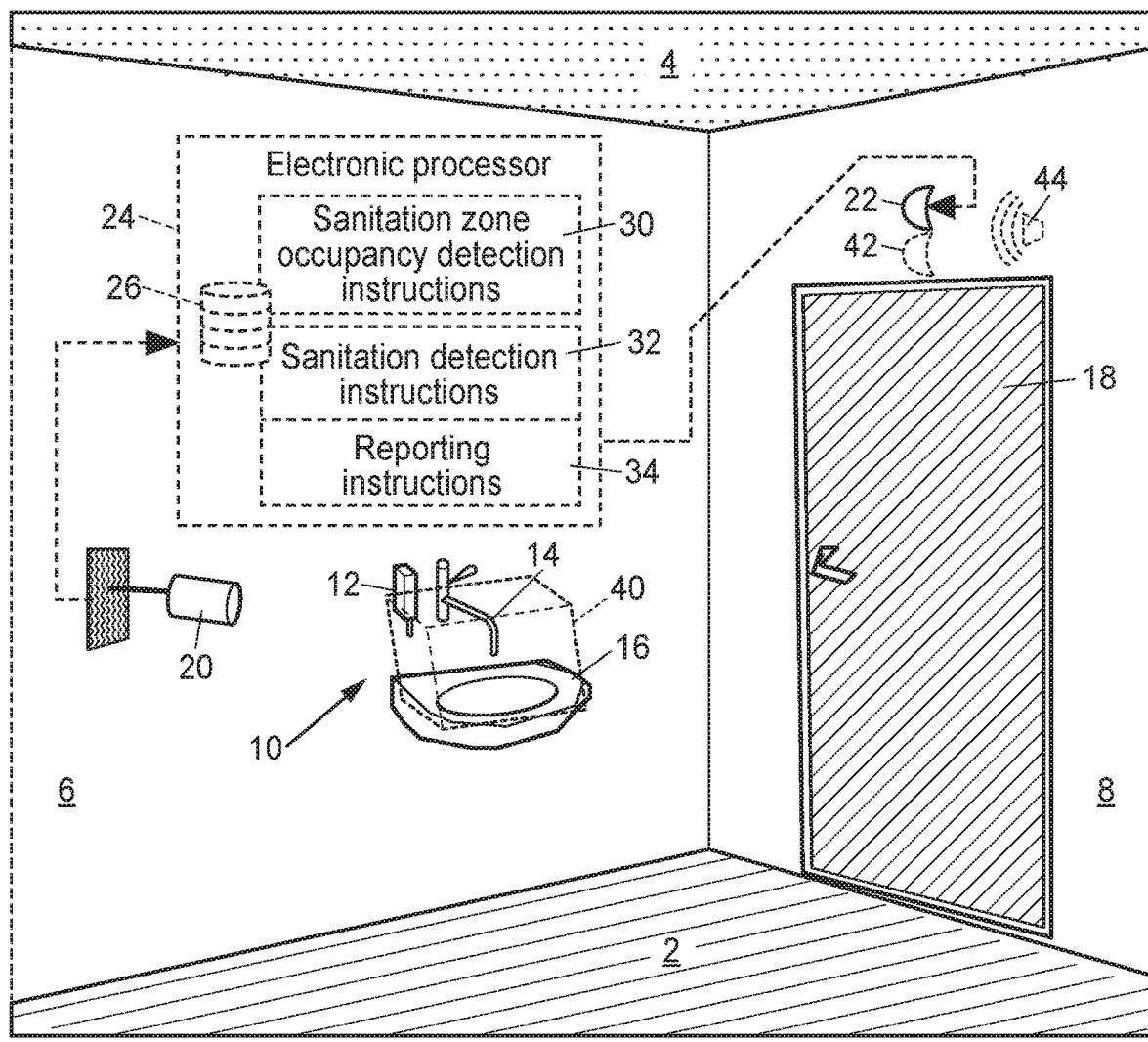
FIG. 1 is a perspective view that illustrates a hand sanitation station in context, along with a hand hygiene protocol enforcement system.

The Figures depict preferred embodiments for purposes of illustration only. Alternative embodiments of the systems and methods illustrated herein may be employed without departing from the principles of the invention described herein.

Any quantitative dimensions shown in the drawing are to be understood as non-limiting illustrative examples. Unless otherwise indicated, the drawings are not to scale; if any aspect of the drawings is indicated as being to scale, the illustrated scale is to be understood as non-limiting illustrative example.

DETAILED DESCRIPTION

Disclosed herein are hand hygiene protocol enforcement systems, devices, instructions (as stored on computer readable medium), and methods which improve compliance with a hand hygiene protocol. The disclosed hand hygiene protocol enforcement directly detects compliance or noncompliance, and provides an immediate and active reminder upon detection of noncompliance, for example in the form of a flashing light and/or audible reminder. Unlike static posted signage which is easily tuned out due to its static ubiquity, the flashing light and/or audible reminder is virtually certain to be noticed. Some embodiments of the disclosed hand hygiene protocol enforcement also leverage group psychology by placing the flashing light in a prominent location so that passers-by are likely to notice it and thereby become aware of the noncompliance event; likewise, an audible alarm can be made sufficiently loud to be heard by passers-by. In this way, it is not necessary to specifically identify noncompliant personnel (although identification of personnel as part of the hand hygiene protocol enforcement is contemplated in some variant embodiments) Likewise, the disclosed hand hygiene protocol enforcement can optionally maintain compliance statistics which are anonymous as monitored individuals are not identified (although, again, in some variant embodiments individuals may be identified and the statistics maintained for individuals). A further advantage of the disclosed hand hygiene protocol enforcement is that it is easily retrofitted to existing hand sanitation stations, and can be added to existing or new hand sanitation stations as an after-market modification.

With reference to FIG. 1, a portion of a room is depicted, including a floor 2, ceiling 4, and walls 6, 8. The room could be a hospital corridor, a hospital ward entranceway, a hospital ward exit hall, a bathroom, a restaurant kitchen, a laboratory hallway, or other such area or room typically used for sanitation or the like. An illustrative hand sanitation station 10 disposed in the room includes two hand sanitation fluid dispensers: a dispenser 12 for providing liquid soap or an antiseptic, antibiotic, antibacterial, alcohol-based, or other specialized hand sanitation fluid, and a water faucet 14. The hand sanitation station 10 further includes a washbasin 16. This is merely an illustrative example, and the hand sanitation station may include numerous additional, fewer, and/or different components. As another example, the hand sanitation station could comprise a soap bar on a soap bar holder, and the illustrative water faucet 14. In this case, the water faucet is the sole sanitation fluid dispenser, and is used in conjunction with the soap bar. Another possible embodiment could include the dispenser 12 for providing an antiseptic, antibiotic, antibacterial, alcohol-based, or other specialized hand sanitation fluid, but not include the water faucet 14 and not include the washbasin 16. The hand sanitation fluid may be a liquid, foam (e.g., hospital foam dispenser), or the like. A sanitation fluid dispenser that dispenses a gaseous sanitation fluid is also contemplated. Furthermore, the hand sanitation station may include a box of gloves or the like, a gown closet for use in a gown-and-glove protocol, or so forth (not shown). FIG. 1 illustrates a typical situation, in which the sanitation station 10 is situated next to or proximate to a door 18 or narrow passage. The hand hygiene protocol typically calls for a person to use the hand sanitation station 10 prior to passing through the door 18. For example, the door 18 could be the entrance to a patient ward in a hospital, and the hand sanitation station 10 is located outside that door so that medical personnel sanitize their hands before entering the patient ward via door 18. Alternatively, the door 18 could be the exit from a patient ward, in which case the hand sanitation station 10 would be located inside the patient ward just prior to reaching the exit door. As yet another example, the door 18 could be the door of a restaurant bathroom, and the hand sanitation station 10 would be the washbasin of the bathroom. A further example, the room of FIG. 1 may comprise a door, a passage way, or portioned out area in a hospital ward or restaurant where each section of the room may be dedicated to a specific patient, specific food based task item, or other specific person, event, or otherwise activity.

With continuing reference to FIG. 1, the illustrative hand sanitation station 10 is augmented by a hand hygiene compliance enforcement device as disclosed herein. The hand hygiene compliance enforcement device includes at least one video camera 20 (and, in some embodiments, only a single video camera 20 as illustrated in FIG. 1, or multiple video cameras (not shown), or, additionally or alternatively, non-camera based sensor(s)), at least one annunciator (in the illustrative example a noncompliance light 22), an electronic processor 24, and a non-transitory storage medium 26 storing instructions 30, 32, 34 that are readable and executable by the electronic processor 24 to process real time video acquired by the at least one video camera 20 in real time.

The video camera 20 is arranged, positioned, or configured such that at least a portion of the hand sanitation station 10 coincides with a wash station zone 40 captured by (i.e. imaged by) real time video acquired by the video camera 20. The wash station zone 40 captured by the video camera 20 (which is only a portion of the full field of view, i.e. FOV, of the video camera 20) thus coincides with the spatial region within which the hand sanitation is expected to be performed by a person using the hand sanitation station 10. In the illustrative example, the wash station zone 40 coincides with the area of the dispenser tip of the hand sanitation fluid dispenser 12, the faucet 14, and the area above the washbasin 16.

The electronic processor 24 and non-transitory storage medium 26 are shown diagrammatically in FIG. 1 by dotted or dashed lines. In physical implementations, the electronic processor 24 may be embodied as a notebook or desktop computer, or as a server computer accessible via the Internet and/or another electronic network (e.g., a public or private local area network (LAN)), or may be embodied as a dedicated electronic component comprising a microprocessor or microcontroller mounted on a printed circuit board (PCB) with ancillary electronics, or so forth. The non-transitory storage medium 26 may be embodied as a hard disk or other magnetic storage medium, a solid-state drive (SSD), flash memory, or other electronic storage medium, an optical disk or other optical storage medium, various combinations thereof, and/or so forth. The non-transitory storage medium 26 may be integrated with the computer or dedicated electronic component implementing the electronic processor 24, e.g. embodied as an internal hard drive or SSD of the computer, or as a read only memory (ROM) other electronic memory chip mounted on the PCB together with the microprocessor or microcontroller. Additionally or alternatively, the non-transitory storage medium 26 may be separate from the computer or dedicated electronic component implementing the electronic processor 24, e.g. embodied as an external hard drive or SSD connected with the computer by a wired or wireless connection, or a network-based storage accessed by the server via the Internet and/or other electronic network. It will be appreciated that the components 24, 26 are shown diagrammatically in FIG. 1, and do not typically occupy the location where they are shown. Rather, they may be located remotely, or may be integrated with the video camera 20 or into the camera mount, or so forth. The electronic processor 24 is operatively connected with the video camera 20 via a wired or wireless connection in order to receive real-time video acquired by the video camera 20. By "real time" video, it is meant that the electronic processor 24 receives and processes the real-time video to identify whether a hand sanitation event occurs (that is, whether a person uses the hand sanitation station 10 to sanitize their hands) and controls the annunciator 22 to annunciate a hand hygiene compliance status based on that determination with sufficiently low time latency that the person perceives he or she is receiving immediate feedback, especially if the person walks past the hand sanitation station 10 without using it. Typically, a time latency of three seconds or less is sufficient, although a time latency of two seconds or less is preferred, and a time latency of one second or less is even more preferable. This high speed computing capacity is readily achieved, for example, if the electronic processor 24 is embodied as a typical commercially available microprocessor or microcontroller such an ARM, Intel, or AMD microprocessor.

As noted, the non-transitory storage medium 26 stores instructions 30, 32, 34 that are readable and executable by the electronic processor 24 to process real time video acquired by the video camera 20 in real time. As diagrammatically indicated in FIG. 1, in the illustrative embodiment the instructions include: occupancy detection instructions 30 readable and executable by the electronic processor 24 to analyze the real time video to determine an occupancy time interval over which a sanitation zone imaged by the real time video is occupied; and sanitation detection instructions 32 readable and executable by the electronic processor 24 to determine whether a hand sanitation event occurs based on images of the wash station zone 40 extracted from the real time video acquired during the occupancy time period and to control the annunciator 22 to annunciate a hand hygiene compliance status based on the determination of whether a hand sanitation event occurs. Reporting instructions 34 may also be provided, which are readable and executable by the electronic processor 24 to accumulate data statistics for a plurality of successive occupancy time periods on corresponding determinations of whether a hand sanitation event occurs and generate a compliance report on the accumulated data statistics.

The annunciator 22 typically includes the aforementioned noncompliance light 22, which is controlled by execution of the sanitation detection instructions 32 to illuminate to indicate detection of noncompliance with the hand hygiene protocol. Typically, the noncompliance light 22 is a red light, although other colors are contemplated herein and may be used. Optionally, the annunciator may include a compliance light 42, e.g. a green light, which is controlled by execution of the sanitation detection instructions 32 to illuminate or to indicate detection of compliance with the hand hygiene protocol (e.g., detection of occurrence of a hand sanitation event). The illustrative lighting annunciators 22, 42 are shown as being placed above the door 18, although they may be placed in some other prominent location where the person entering the door 18 is unlikely to miss them. Additionally or alternatively, the annunciator may be implemented as an audio speaker 44 which is controlled by execution of the sanitation detection instructions 32 to output a verbal reminder to use the hand sanitation station 10 in response to detection of noncompliance with the hand hygiene protocol. Other annunciator devices are additionally or alternatively contemplated, such as a display that displays a textual and/or graphical reminder to use the hand sanitation station 10 in response to detection of noncompliance with the hand hygiene protocol. In lighting or display annunciators, illumination may be accomplished by a flashing illumination (especially in the case of the noncompliance annunciator light 22), or, in the case of a display, showing or displaying the textual and/or graphical reminder as a flashing text and/or flashing graphic.

Figure 2:
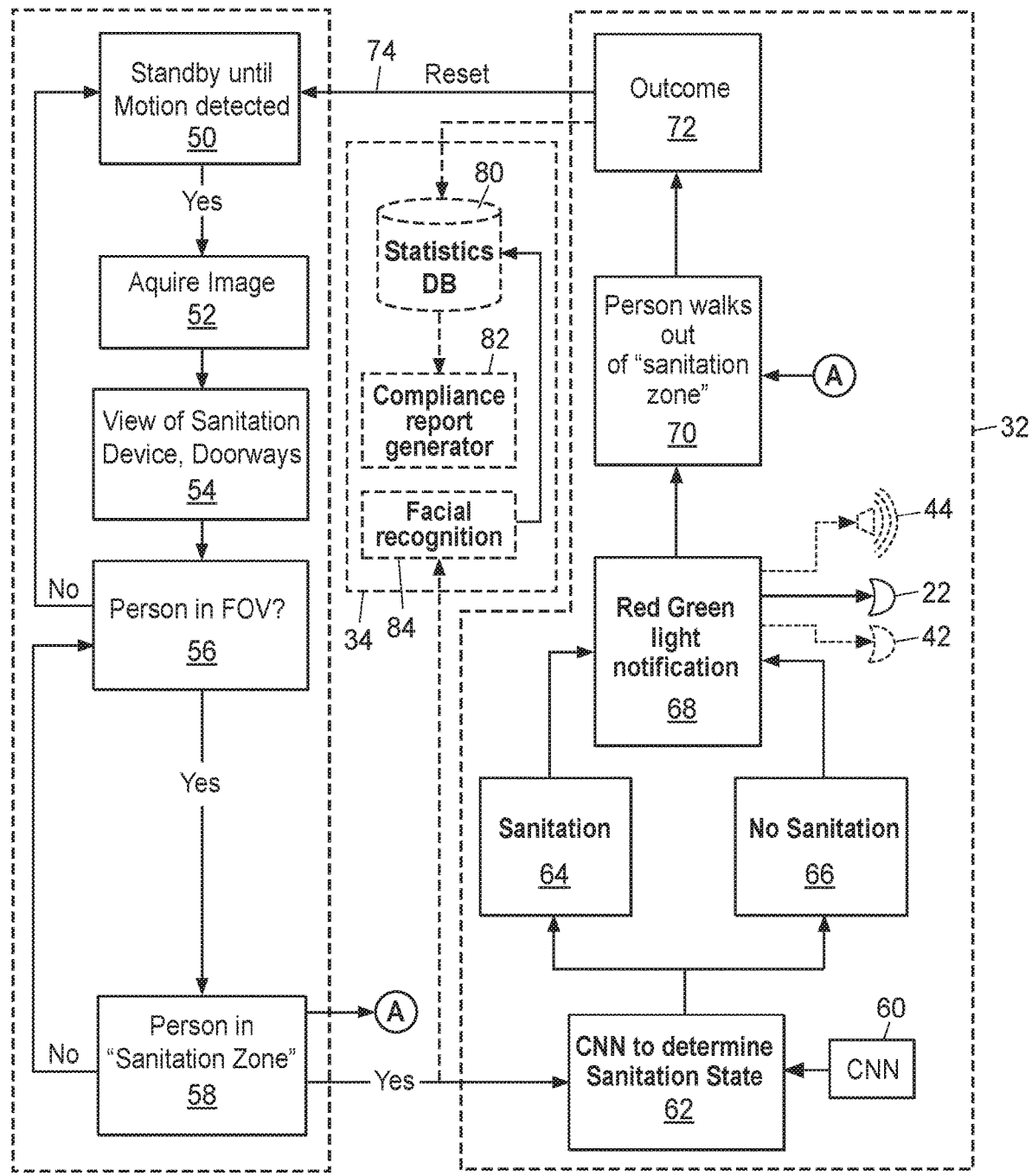
FIG. 2 is a flow diagram that diagrammatically illustrates operation of the hand hygiene protocol enforcement system of FIG. 1.

With reference now to FIG. 2, some illustrative hand hygiene compliance enforcement methods suitably implemented by the hand hygiene compliance enforcement device of FIG. 1 are described. In illustrative FIG. 2, method operations indicated by blocks are enclosed by dashed lines indicating operations performed by the occupancy detection instructions 30, the sanitation detection instructions 32, and the reporting instructions 34, respectively. However, it is to be appreciated that these are merely illustrative allocations, and that more generally the hand hygiene compliance enforcement method may be encoded using different organizational arrangements. More generally, the non-transitory storage medium 26 stores instructions 30, 32, 34 are readable and executable by the electronic processor 24 operatively connected with the at least one video camera 20 and at least one annunciator 22, 42, 44, and are executable by the electronic processor 24 to process real time video acquired by the at least one video camera 20 in real time to perform the disclosed hand hygiene compliance enforcement methods.

Additionally, or alternatively, with respect to FIG. 1, one or both of electronic processor 24 and non-transitory storage medium 26, may be dynamically shared, controlled, and/or utilized through a local collection of devices. In such embodiments, electronic processor 24 and/or non-transitory storage medium 26, as diagrammatically illustrated in FIG.

1 by dotted or dashed lines, may be connected within a local network and/or controlled in a network-based storage. For example, the physical components 24, 26 may be fully integrated into a device that physically holds the video camera 20, hand sanitation station 10, and/or other stated components in FIG. 1. Such embodiments utilize the electronic processor 24 to connect with the video camera 20 in order to receive real-time video acquired by the video camera or some type of "video like sensor." This could receive and process video to identify whether a hand sanitation event occurs and control the annunciator 22 to annunciate a hand hygiene compliance status among other embodiments. Additionally, or alternatively, the non-transitory storage medium 26 may be separate from the computer or dedicated electronic component implementing the electronic processor 24. As noted above, the non-transitory storage medium 26 stores instructions 30, 32, 34 that are readable and executable by the electronic processor 24 to process real time video acquired by the video camera 20 in real time. In various embodiments herein, the non-transitory storage medium can be dynamically changed, and by local or internet connected containers that serve as a system of structure to share, compute and hold sanitation zone occupancy detection instructions 30, sanitation detection instructions 32, and reporting instructions 34. Such node-based system could further pool and share resources from local electronic processors 24, but host those resources via the internet or other connection, this embodiment would further aid in computational ability for "real time" video and further add the ability for local inference. Such based node system would host and allocate through the physical 24 electronic processor or the node processing power to execute the detection instructions 30, sanitation detection instructions 32, reporting instructions 34 to, e.g., accumulate data statistics. In such embodiments, the processor 24, non-transitory storage medium 26, and/or related instructions may comprise, or be part of, a cloud based platform, network, or system.

In the illustrative example of FIG. 2, in an operation 50 the hand hygiene compliance enforcement method remains in standby until motion is detected. For example, the video camera 20 may continuously acquire video and a difference image generated for each successive frame by subtracting the immediately preceding frame (or some earlier frame, e.g. the second-most immediate frame) from the current frame. In the absence of motion, this difference image should have no content; if motion is occurring then the difference image will have content corresponding to the change in image content caused by the motion. Motion is then detected if the sum of pixel values over the area of the difference image is greater than some threshold value. This is merely an illustrative example, and other types of camera-based motion detection are contemplated. As a variant embodiment, it is contemplated to provide a separate motion sensor (not shown) to perform the operation 50, e.g. a laser beam that is broken to detect passage of a person.

Upon detection of motion in the video, process flows to operation 52 where an image is acquired (or, alternatively, the most recent video frame processed in operation 50 is used). At this stage, an image area 54 is considered, which includes the portion of the image depicting the sanitation station 10, the door 18, and closely adjacent area. In an operation 56, image analysis is performed on the image area 54 to confirm that the detected motion is due to a person being in the image area 54. This analysis may, for example, entail computing a difference image for the area 54 comparing the image from operation 52 with earlier frames for which no motion was detected in operation 50, or alternatively computing the difference image respective to a stored reference image of the image area 54. Any suitable image analysis technique for detecting a person in an image can be employed, e.g. connectivity analysis may be performed on the difference image to detect object size and aspect ratio which is compared with expected size and aspect ratios for typical human beings. If no person is detected, flow returns to operation 50 to continue monitoring the video for motion detection.

On the other hand, if the operation 56 confirms a person is in the image area 54, then in an operation 58 it is determined whether a sanitation zone is occupied by the person. The sanitation zone is an area within the area 54 which corresponds to the person being sufficiently proximate to the sanitation station 10 that the person would be expected to be using the sanitation station 10 prior to passing through the door 18. Preferably, the sanitation zone extends from the spatial point where a person might first be close enough to use the sanitation station 10 to the spatial point where the person has fully passed the sanitation station 10 such that it becomes apparent that the person has bypassed the sanitation station 10. Various approaches can be used to determine the occupancy. For example, for successive frames of the real time video, an image of the sanitation zone can be extracted from the frame and compared with a reference image of the sanitation zone to detect whether the extracted image of the sanitation zone indicates occupation of the sanitation zone. Additionally or alternatively, for successive frames of the real time video, an image of the sanitation zone can be extracted from the frame. The images of the sanitation zone extracted from the successive frames of the real time video are then compared to detect frame-to-frame changes that indicate occupation of the sanitation zone. Again, each of these are merely illustrative examples.

With conditioned reference to FIG. 2 any portion of the sanitation detection instructions 32, the reporting instructions 34, and/or occupancy detection instructions 30 could be broken out of the their respected "dotted lines'. These lines with the use of a local node of cloud computation can be broken out and separated if desired. Each logic block on FIG. 2 could be exchanged between CPU and/or GPU, and/or a cloud based computation back end to complete the overall cycle or implementation of the instructions described herein for each of the sanitation detection instructions 32, the reporting instructions 34, and/or occupancy detection instructions 30.

Although not explicitly depicted in FIG. 2, it is to be understood that this process may be performed for successive frames of the real-time video to determine an occupancy time interval over which a sanitation zone imaged by the real time video is occupied. It is further noted that the successive frames are not necessarily immediately adjacent in the video stream. For example, if the video camera 20 is operating at a standard rate of 30 fps (i.e. frames-per-second), the successive frames could, for example, be every fifth acquired frame (so that the successive frames actually analyzed would be at a rate of 6 fps). The choice of whether to analyze every frame, or every second frame, or every fifth frame, or so forth is suitably made to balance processing speed versus temporal resolution. For example, processing every frame provides 30 fps→30 Hz temporal resolution but requires processing speed to handle processing each frame in $1/30^{th}$ of a second; whereas, processing every fifth frame provides coarser temporal resolution of 6 fps→6 Hz, but only requires processing speed to handle processing each frame in $1/6^{th}$ of a second.

With continuing reference to FIG. 2, upon detection at operation 58 of occupancy of the sanitation zone, execution of the sanitation detection instructions 32 by the electronic processor is triggered in order to determine whether a hand sanitation event occurs based on images of the wash station zone 40 extracted from the real time video acquired during the occupancy time period and to control the at least one annunciator 22, 42, 44 to annunciate a hand hygiene compliance status based on the determination of whether a hand sanitation event occurs. In the illustrative example, the detection of whether a hand sanitation event occurs is performed using a Convolutional Neural Network (CNN), however it is to be understood that other artificial intelligence (AI) based network(s) or algorithms, e.g., comprising a neural network structure, may be used. In various embodiments, CNN 60 may be pre-trained to generate a confidence value as to whether a hand sanitation event is depicted in an image of the wash station zone using training images of the wash station zone that depict a hand sanitation event and training images of the wash station zone that do not depict a hand sanitation event. More generally, other supervised, semisupervised, or unsupervised machine learning (ML) classifiers can be used for estimating whether a hand sanitation event is depicted in the image. For example, a machine learning model, CNN, or other AI model as described herein, may be trained using a supervised or unsupervised machine learning program or algorithm. The machine learning program or algorithm may employ a neural network, which may be a convolutional neural network, a deep learning neural network, or a combined learning module or program that learns in two or more features or feature datasets in a particular areas of interest. The machine learning programs or algorithms may also include natural language processing, semantic analysis, automatic reasoning, regression analysis, support vector machine (SVM) analysis, decision tree analysis, random forest analysis, K-Nearest neighbor analysis, naïve Bayes analysis, clustering, reinforcement learning, and/or other machine learning algorithms and/or techniques. Machine learning may involve identifying and recognizing patterns in existing data (such as hand sanitation events as determined from pixel or sensor data as received from video cameras or non-camera-based sensors as described herein) in order to facilitate making predictions for subsequent data (e.g., to predict whether a hand sanitation event has occurred).

Machine learning model(s), such as those of a machine learning model, CNN, or other AI model as described herein, may be created and trained based upon example (e.g., "training data,") inputs or data (which may be termed "features" and "labels") in order to make valid and reliable predictions for new inputs, such as testing level or production level data or inputs. In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, or otherwise machine learning "models" that map such inputs (e.g., "features") to the outputs (e.g., labels), for example, by determining and/or assigning weights or other metrics to the model across its various feature categories. Such rules, relationships, or otherwise models may then be provided subsequent inputs in order for the model, executing on the server, computing device, or otherwise processor(s), to predict, based on the discovered rules, relationships, or model, an expected output.

In unsupervised machine learning, the server, computing device, or otherwise processor(s), may be required to find its own structure in unlabeled example inputs, where, for example multiple training iterations are executed by the server, computing device, or otherwise processor(s) to train multiple generations of models until a satisfactory model, e.g., a model that provides sufficient prediction accuracy when given test level or production level data or inputs, is generated. The disclosures herein may use one or both of such supervised or unsupervised machine learning techniques.

With reference to FIG. 2, to generate the training images, video (having pixel data) or sensor information (having sensor data) is taken or collected of various people passing through the sanitation zone who do, or do not, use the sanitation station 10. This approach for training the CNN 60 (or other ML classifier) requires collection of the training images or sensor data at the site where the sanitation station 10 is deployed.

Alternatively, the training may use training images or sensor data of a standard wash station zone that depict a hand sanitation event and training images of the standard wash station zone that do not depict a hand sanitation event. To generate training images or sensor data, video is taken, or sensor data is collected, of various people passing through the sanitation zone of a standard sanitation station (preferably of the same manufacture and model as the sanitation station 10 at which the compliance enforcement device is to be deployed) who do, or do not, use the standard sanitation station. This approach advantageously allows for the pre-trained CNN (or other ML classifier) 60 to be shipped with the compliance enforcement device and eliminates the need to perform on-site training of the CNN.

Rather than using the CNN 60, another type of ML classifier could be used, such as another type of artificial neural network (ANN), or a support vector machine (SVM) classifier, or another architecture such as VGG, ResNET, RCNN, MaskRCNN, MobileNET, Inception family or so forth. In another approach, the CNN 60 is trained to employ Human Pose estimation, in which the CNN 60 is trained on key points that align to human body parts such as the right elbow, left knee, and so forth. Using a CNN for Human Pose estimation advantageously allows for deriving when a hand sanitation action would occur. In tests, this approach was significantly more computationally heavy and less accurate, making real time inference difficult. Additionally or alternatively, a local node of cloud computation can be used, which may allow the systems and/or methods of FIG. 2 to become more feasible. This Human Pose estimation could be further aggregated (e.g., via an aggregation method as described herein), or used in conjunction with other embodiments described herein, to decide the gate and posture of the person. The ML classifier could also employ a semi- or unsupervised approach. A variable autoencoder or Generative Adversary Network (GAN) could be used to train two competing networks to train towards creating different hand sanitation depictions. This could then be used as training for a model or inference side comparing the GAN's likelihood of possibility value to compare to currently acquired images.

With continuing reference to FIG. 2, at an operation 62 for each frame of successive frames of the real time video acquired during the occupancy time period, the CNN is applied to the image of the wash station zone extracted from the frame in order to generate a confidence value indicative of likelihood that the image of the wash station zone depicts a hand sanitation event. A determination is made of whether a hand sanitation event occurs in the wash station zone based on the confidence values for the successive frames. This determination may be either (1) a hand sanitation event occurs 64; or (2) a hand sanitation event does not occur 66. At an operation 68, the annunciator 22, 42, 44 is controlled to annunciate a hand hygiene compliance status based on the determination of whether a hand sanitation event occurs. This process continues until, at an operation 70, it is determined (via continued execution of the occupancy detection instructions 30) that the person walks out of the sanitation zone, thereby ending the occupancy time interval. At an operation 72, the final outcome (either a hand sanitation event occurred over the occupancy time interval, or it did not) is determined. Optionally, this may trigger a further annunciation, e.g. if there has been no compliance then the noncompliance light 22 may be set to a flashing illumination, or if the audio speaker 44 is provided at this point an audible reminder may be issued to use the sanitation station 10. The outcome operation 70 also triggers a reset 74 of the occupancy detection instructions 30 to reset the hand hygiene compliance enforcement device for the next person.

In the illustrative example of FIG. 2, the annunciator 22, 42, 44 is controlled at the operation 68 to annunciate the hand hygiene compliance status in an ongoing fashion over the course of the person's progress through the sanitation zone. Hence, as the person enters the sanitation zone this is detected at operation 58, and as initially the person will not have used the sanitation station 10 the output of operation 62 is no sanitation 66 and the (e.g. red) noncompliance light 22 will be illuminated at operation 68. Optionally, this may also trigger an initial audible reminder via the audio speaker 44 (if provided) that the sanitation station 10 should be used before entering the door 18. If at some point the person uses the sanitation station 10 then this will be detected at operation 62 causing the output will to switch to compliance 64 and the noncompliance light 22 will be turned off and the (e.g. green) compliance light 42 (if provided) is turned on. On the other hand, if the person completes passage through the sanitation zone without using the sanitation station 10 then the outcome operation 70 optionally records the noncompliance and/or optionally issues a final reminder, e.g. by causing the noncompliance light 22 to flash and/or issuing a final audible reminder via the loud speaker 44. More generally, in this embodiment the noncompliance light 22 is controlled to illuminate starting at the beginning of the occupancy time interval and ending at the earlier of (i) a stop time respective to the end of the occupancy time interval or (ii) a time when it is determined that a hand sanitation event occurs. The stop time is typically set to be a second or so up to a few seconds after the end of the occupancy time interval so as to remain illuminated until the person has, most likely, passed through the door 18. This approach has certain advantages, such as providing an immediate reminder via illumination of the noncompliance light 22 (and the optional audible reminder) that the person should use the sanitation station 10.

In a variant annunciation approach, the audible initial reminder via the loud speaker 44 (if provided) may initially be provided as the person enters the sanitation zone, but the noncompliance light 22 is not initially activated. Thereafter, as the person passes through the sanitation zone no annunciation is provided (e.g., neither light 22, 42 is lit, nor is any audible annunciation output). If at some point the person uses the sanitation station 10 then this will be detected at operation 62 causing the (e.g. green) compliance light 42 (if provided) is turned on. On the other hand, if the person completes passage through the sanitation zone without using the sanitation station 10 then the outcome operation 70 illuminates the non-compliance light 22 (for the first time, in this embodiment) to remind the person of his or her non-compliance, and/or issues an audible reminder via the loud speaker 44. This approach provides a more delayed response, but has certain advantages. For example, in this embodiment the red light 22 only illuminates if the person passes completely through the sanitation zone without using the sanitation station 10. In other words, the red light 22 only illuminates if the person has failed to use the sanitation station 10. This embodiment advantageous leverages social pressure to encourage enforcement with the hand hygiene protocol, because if the red light 22 illuminates then any person in the area who sees it will know the person approaching the door 18 has failed to use the sanitation station 10.

Setup of the hand hygiene compliance enforcement device may be done at some time after the sanitation station 10 is installed, and proceeds as follows. The video camera 20 and annunciator(s) 22, 42, 44 are installed, and the electronic processor 24 and storage 26 are installed and operatively connected with the video camera 20 and annunciator(s) 22, 42, 44. These connections may be by way of physical wires or cables, or by wireless connections (e.g., Bluetooth™, WiFi, et cetera). The software 30, 32, 34 can be installed, or, can come preinstalled on the storage medium 26. Next, the area 54 (see FIG. 2), the sanitation zone, and the wash station zone 40 (see FIG. 1) are defined. In one approach, this is done by taking test video frames and displaying them on a computer display, cellphone, or the like. An installer may need to adjust the positioning of the video camera 20 to ensure it is fully capturing at least the sanitation zone (and hence the wash station zone 40 located inside the sanitation zone). When the video camera 20 is properly positioned, the installer acquires video and displays a frame on the display, and manually (e.g. using a mouse, touch-sensitive screen, or the like) defines boxes in the frame defining the wash station zone and the larger sanitation zone (and the still larger image area 54, unless this area 54 coincides with the sanitation zone). In some embodiments, additionally or alternatively, a touch-sensitive screen, such as a touchscreen display, may be used to display hand sanitation messages. In such embodiments, a touchscreen display may be installed or positioned as an annunciator alone or with other annunciator(s) described herein, including, for example any one or more of annunciator(s) 22, 42, 44. That is, a touchscreen display may be used as a substitution to, or addition to, the compliance lights 22 and/or 42, or audio speaker 44. In some embodiments, a touchscreen display may include a digital green and red lights or similar animations or visual feedback. Additionally, or alternatively, a touchscreen display could hold animations and visuals combined with verbal or audio sound for prompting positive behavior (e.g., hand washing compliance). Additionally, or alternatively, hand sanitations messages can include one or more positive messages instructing a user to wash his or hands and keep safe. Additionally, or alternatively, hand sanitations messages may further comprise an animation, clock, or other depictive functional and/or non-functional graphics corresponding to a user's hand washing session or compliance. In various embodiments, a touchscreen display may be configured to turn on when a person passes a sanitation zone in order to encourage the person to sanitize his or her hands. In some embodiments, the touchscreen display may allow the user to input a command (e.g., a verbal or physical command) to indicate compliance. Such features may assist users that may be forgetful to use the hand hygiene compliance enforcement device (e.g., at critical locations, including entry into a sensitive area), which can increase effective sanitation rates overall.

In various embodiments, the annunciator(s) 22, 42, 44, and/or a display or touchscreen display may be used for sanitation "information sharing." Information sharing comprises sharing information within a proximity to a hand hygiene compliance enforcement device, or portion thereof. The information may be shared, e.g., via a touchscreen display or display viewable by people) in the vicinity of the hygiene compliance enforcement device, or portion thereof. Such public display would invoke "information sharing" to encourage individuals, who are not bound (e.g. legally bound) by compliance, such as hospital visitors and others, to nonetheless engage in positive hand sanitation behaviors. For example, unlike, doctors, nurses, and hospital staff, or restaurant workers or lab workers, individuals not required to comply with hand sanitation regulations may fail to comply with hand sanitation, without social pressure as caused by an "information sharing" annunciator, such as a display screen showing a given individual's hand sanitation compliance. By centralizing, or making available, the dissemination of simple information at or near a hand hygiene compliance enforcement device, or portion thereof, information sharing on display devices (or other annunciator(s) as described herein) may cause persons in public spaces that incorporate these device(s) to comply with sanitation regulations, thereby increasing hand sanitation compliance overall. For example, in an embodiment, a touchscreen display may be used to share information about a given hospital's hand sanitation compliance, e.g., time, rating, and positive reports regarding hand sanitation that the hospital would could then share with customers, patients, etc. By sharing such information on a display or screen, near a hand hygiene compliance enforcement device, or portion thereof, such information would further encourage positive hand sanitation protocol(s). As a further example, a restaurant may use a screen to share information about sanitation compliance, including the restaurant's use of menus, QR codes, or other touchless payment types that demonstrate restaurant compliance with certain disease protocols (e.g., COVID-19). As a further example, and in general, public spaces, such as museums, co-working spaces, or locations where many people gather, could have installed an information sharing system, as described herein, to not only share compliance "guidelines," but also to determine who is (and how many people are) are complying, whether it be outside or inside of legal compliance. Such embodiments provide the advantage of increasing compliance because, as demonstrated in these examples, such embodiments may lead to reduced "sanitation leakage," especially in places where a lack of sanitation could occur because of a typical lack of tracking or monitoring. Accordingly, use of a hygiene compliance enforcement device, or portion thereof, in such locations may cause increased sanitation, and related statistics, and better metrics overall.

In various embodiments, information sharing data or information may be stored in statistics database 80, or in other computer memorie(s) associated with electronic processor such as a non-transitory storage medium 26. The information sharing data or information may be reported as described herein, via reporting instructions 34 and/or compliance report generator 82. In further embodiments, a hand hygiene compliance enforcement device may be configured to control information sharing through an application (app), which may comprise one or more computing instructions stored in non-transitory storage medium 26, and configured for execution on electronic processor 24. The application may be a native app, such as an APPLE iOS app or a GOOGLE ANDROID app. The information sharing app could comprise an information sharing interface as implemented or displayed on a mobile device (e.g., smart phone or tablet) or could comprise a webpage of a website. The information sharing interface could provide data or statistics for information sharing, as described herein, to a display screen, e.g., via reporting instructions 34 and/or compliance report generator 82. In this way, such information sharing data or statistics may be provided to a hygiene compliance enforcement device or, additionally or alternatively, to a group of devices (e.g., mobile devices) via one or more corresponding information sharing interface(s). By using the information sharing interface(s), a customer or any person that wants to view or share information regarding hand sanitation compliance could access an information sharing interface, e.g., by downloading an app, uploading an image, uploading a video, or sharing text content, to provide and/or monitor hand sanitation compliance of a particular zone or location, even a location remote to the hygiene compliance enforcement device or the user.

In some embodiments, information sharing and display, e.g., via information sharing interface(s) as described herein, may comprise displaying notifications, marketing, advertisements, or the like. In such embodiments, "marketing verification inference analysis" may be provided as, or with, hand sanitation messages or other notifications as described herein. In particular, tracking marketing inferences in a physical marketing environment is typically difficult for marketers. Through hand sanitation compliance, as described herein, however, tracking inference and physical presence of individuals could be implemented by use of hand hygiene compliance enforcement devices as described herein. For example, display of advertisement(s) and related tracking as to one or more marketing inference(s) across one or more users may be stored on statistics database 80, or in other computer memorie(s) associated with electronic processor such as a non-transitory storage medium 26. The display and/or tracking may be implemented though the hand sanitation techniques as described herein. For example, the annunciators and related imaging analysis, such as provided via a display and/or touchscreen display, which may be in a proximity to a hand sanitation zone and/or device as described herein, may be used for such tracking.

Figure 4:
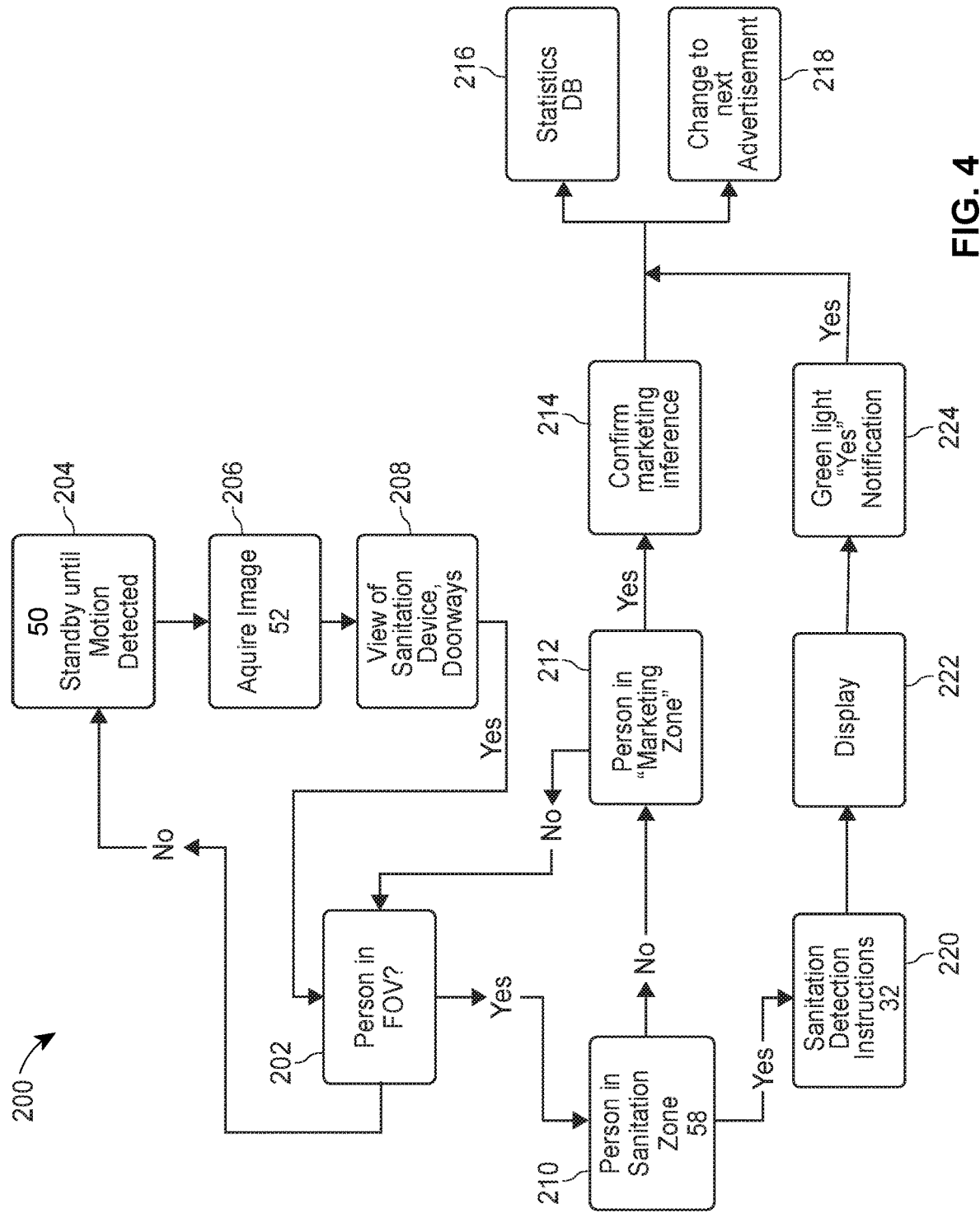
FIG. 4 illustrates a flowchart of the hand hygiene protocol enforcement system of FIG. 1 used to provide marketing based information sharing.

For example, FIG. 4 illustrates a flowchart of the hand hygiene protocol enforcement system of FIG. 1 used to provide marketing based information sharing. In the example of FIG. 4, at block 202 a hand hygiene protocol enforcement system may determine whether a person is in a field of view (FOV) of a camera or non-camera based sensor as described herein. If no person is detected, at block 204, the hand hygiene protocol enforcement system may standby until motion is detected. The hand hygiene protocol enforcement system may then continue to acquire images (206) of the related environment, including the view of the sanitation device, doorways, etc. (208). If a person is detected, at block 210, the hand hygiene protocol enforcement system determines that a person is in the sanitation zone. The example of FIG. 4 comprises a "marketing zone," which is an area near or around, and is typically larger than, the sanitation zone of the hand hygiene protocol enforcement system (e.g., the hand hygiene compliance enforcement device) as described herein. The marketing zone defines an area from which individuals can view, e.g., a touchscreen or display screen, and potentially be shown or served an advertisement. In some embodiments, the marketing zone may be a pass-by area that can serve or show advertisements in a vicinity of the hand hygiene protocol enforcement system (e.g., the hand hygiene compliance enforcement device). In instances (212) where the hand hygiene protocol enforcement system determines that a person is not in the sanitation zone, but is in a marketing zone, a confirmation of a marketing inference (214), e.g., presence of the person, can be determined and tracked by the hand hygiene protocol enforcement system. Alternatively, in instances (220) where a person is in the sanitation zone, then an annunciator, such as a display (222), or green or red light (e.g., 22 and/or 42, respectively) (224), may be used to confirm that a person in a proximity to the hand hygiene protocol enforcement system during a time when a marketing advertisement was shown. In this way, for example, a screen or display may encourage hand sanitation, and at the same time, may be used to provide or show advertisements. In such embodiments, a portion, e.g., small partition, of a screen or display may be used for advertising space. In other embodiments, utilizing multiple screens or displays may be used, where one screen may show animations, green or red lights, or other hand sanitation related information and/or graphics, but where another screen may show adertisements. In such embodiments, either way, occupation of either the marketing zone or sanitation zone would cause a confirmation of an individual being present for the display of an advertisement. Such information, as to one or more marketing inference(s), may be tracked and stored on statistics database 80 (216), or in other computer memorie(s) associated with electronic processor such as a non-transitory storage medium 26. Tracking may allow advertisements to be rotated or changed over time (218) for specific users and/or specific locations.

These advertisements can be controlled through a hand hygiene marketing platform, which may be implemented on the hand hygiene compliance enforcement device described herein. The platform can comprise a sanitation marketing application that connects marketers through the hand hygiene compliance enforcement device. The hand hygiene marketing platform may be configured to control marking through a marketing application (app), which may comprise one or more computing instructions stored in non-transitory storage medium 26, and configured for execution on electronic processor 24. The hand hygiene marketing platform could comprise a marketing interface as implemented or displayed on a mobile device (e.g., smart phone or tablet) or could comprise a webpage of a website, or native app as described herein. The marketing interface provides data or statistics for providing advertisement, as described herein, to a display screen, e.g., via reporting instructions 34 and/or compliance report generator 82. In this way, such advertisements may be provided to a hygiene compliance enforcement device or, additionally or alternatively, to a group of devices (e.g., mobile device) via one or more corresponding display or screen interface(s).

In various contemplated approaches, a CNN or other ML architecture can be used to define the wash station and sanitation zones, e.g. the CNN 60 could be another type of ANN, or an SVM classifier, or could be trained to employ Human Pose estimation, or so forth. Finally, as previously noted, the CNN (or other ML classifier) 60 is pretrained to generate the confidence value using training images of the wash station zone or a standard wash station zone that depict a hand sanitation event and training images of the wash station zone or the standard wash station zone that do not depict a hand sanitation event. If training images of a standard wash station zone are used, then the pretrained CNN 60 comes preloaded with the sanitation detection software module 32. On the other hand, if training images of the wash station zone 40 of the sanitation station 10 are to be used in the training, then the installer collects the requisite training data. Preferably, the training data are collected using a number of different people capturing the expected range of human variation (height, weight, skin tone, et cetera) commensurate with the full range of people expected to be using the sanitation station 10. In this latter case, the loaded software includes the CNN training software so that the CNN 60 can be trained on the just-collected training images. Finally, the installer tests the compliance enforcement system using several test runs (again, preferably with people of different heights, weights, skin tones, et cetera) to verify accuracy of the compliance enforcement system.

With continuing reference to FIG. 2, optionally, the reporting instructions 34 are provided to generate statistical compliance data. To this end, a statistics database 80 collects the outcomes 72, and an operation 82 generates a compliance report based on inputs received from a user at the electronic processor 24, e.g., the user may select via a keyboard, mouse, or other user input device to generate a compliance report for the sanitation station 10 over some user-selected time interval, and optionally may further narrow the report to a certain work shift or so forth. The hand hygiene compliance enforcement device does not identify the persons whose compliance is monitored—accordingly, the generated compliance report is anonymous. However, it is contemplated, for some embodiments, to group the outcomes 72 in various ways to provide more targeted statistics. For example, the outcomes 72 can be grouped based on the ward or other locational groupings. The outcomes 72 can also be grouped based on the time of event. For example, if the hospital runs three work shifts with defined work shift change times, then the statistics can be grouped by work shift to assess compliance for each work shift. The outcomes 72 can additionally or alternatively be grouped by worker type, based on analysis of the image area 54. For example, different types of hospital workers (e.g. nurses, orderlies, doctors) can be distinguished based on types of uniform (or lack of a uniform). Alternatively, if hospital workers are required to wear radio frequency identification (RFID) badges, then an RFID reader may be incorporated into the hand sanitation compliance monitoring system to identify classes of workers. In this way, compliance can be assessed for different types of workers. As a further variant on this, in some cases visitors may not be required to perform hand sanitation before entering a ward. In this case, analysis of the image area 54 can be used to identify visitors (e.g., based on lack of uniform, or by detecting a "Visitor" badge in the image area 54 or, if the "Visitor" badge includes an RFID tag, by incorporating an RFID tag reader to identify the person as a visitor based on the tag reading) and discard outcomes for visitors. (This information may also optionally be fed to the notification operation 68 in order to avoid annunciating a hand hygiene compliance status in the case of visitors). Conversely, if the hospital employs RFID badges for employees but not for visitors, then any person identified in the sanitation zone in operation 58 who does not also register on the RFID tag reader may be designated as a visitor and the corresponding outcome discarded.

With continuing reference to FIG. 2, in a variant embodiment the reporting instructions 34 further implement facial recognition 84, or alternatively issue calls to a facial recognition module, whereby video frames acquired over the course of the occupancy time period are processed by the facial recognition to compare against a facial database in an effort to identify the person. If the person is recognized, then the outcome stored in the statistics database 80 is annotated with the person's identification. In this case, the compliance report generated at the operation 82 may be sorted by name, so that persons with poor compliance can be individually identified. Optionally, in this variant embodiment it is also contemplated for the annunciator, if embodied at least in part as a loud speaker 44 or display, to identify the individual when annunciating the hand hygiene compliance status at the outcome 70. In a variant approach, if the hospital employs an RFID badging system then an RFID reader may be incorporated into the hand sanitation compliance monitoring system to identify individuals.

Figure 3:
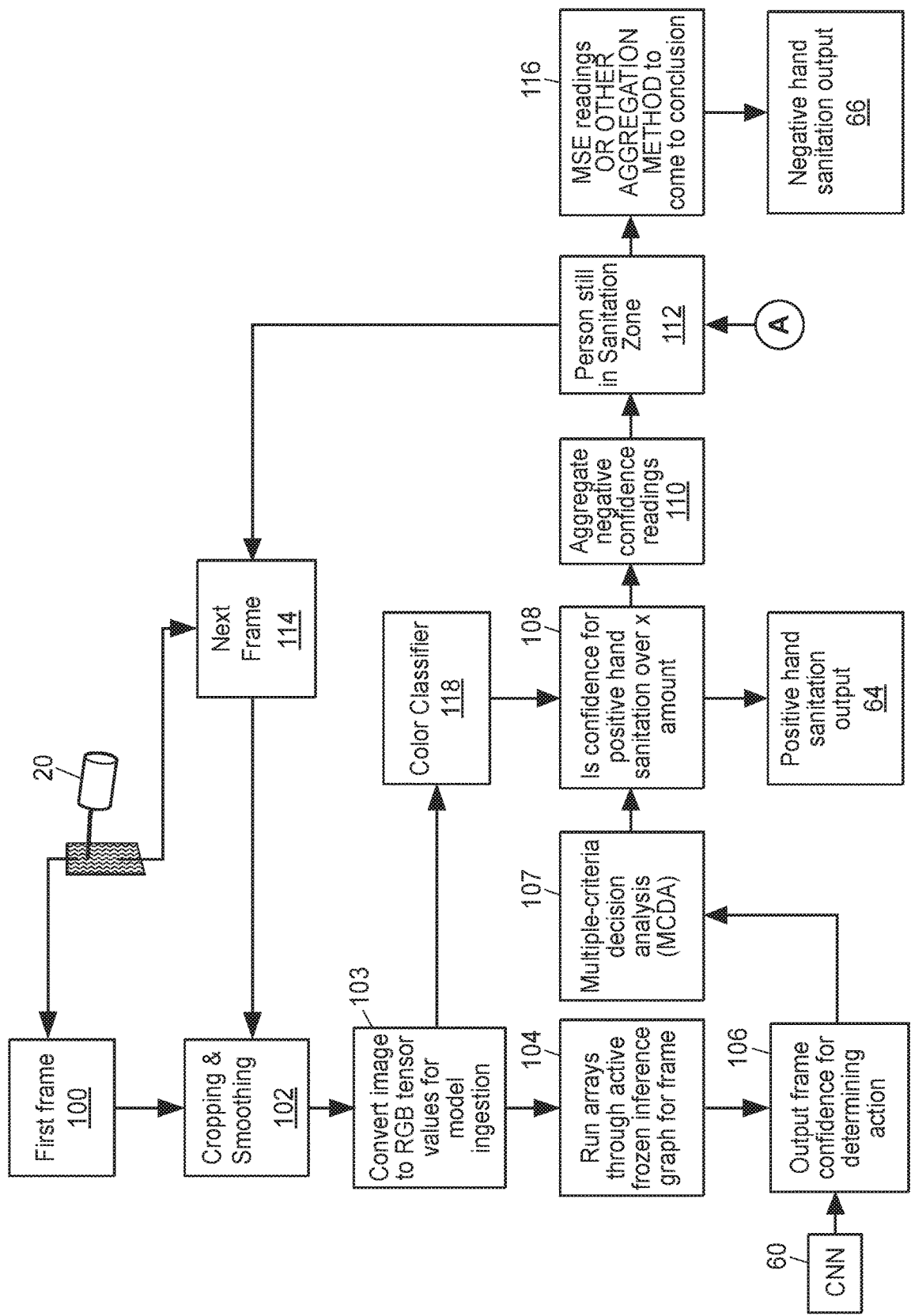
FIG. 3 is a flow diagram that diagrammatically illustrates operation of the sanitation state determination operation of FIG. 2.

With reference now to FIG. 3, an illustrative embodiment is described of the operation 62 in which, for each frame of successive frames of the real time video acquired during the occupancy time period, the CNN (or other ML classifier) 60 is applied to the image of the wash station zone extracted from the frame in order to generate a confidence value indicative of likelihood that the image of the wash station zone depicts a hand sanitation event. A first frame 100 is received from the video camera 20. In an operation 102, the image of the wash station zone 40 is extracted from the frame 100, and may optionally be further processed, for example by pixel resampling to modify the spatial resolution. For efficient processing, the extracted image of the wash station zone is preferably relatively small. In one illustrative example, the video frame 100 is 1280×720 pixels in size (i.e., 1280 by 720 pixels), and the extracted image of the wash station zone (after optional pixel resampling) is on the order of 72×72 pixels (i.e., 72 by 72 pixels) to 84×84 pixels (84 by 84 pixels) in size, although larger or smaller sizes are contemplated. In some embodiments, the image of the wash station zone extracted in the operation 102 (including optional resampling) has pixel dimensions length by width, i.e., L×W (L by W) where L is 100 pixels or less and W is 100 pixels or less. This has two advantages. First, the relatively small number of pixels provides for efficient processing, which facilitates real-time analysis of the video on a frame-by-frame basis. Second, and counterintuitively, it is expected that pixel resampling to a coarser resolution having a smaller number of pixels (e.g. in the 100×100 pixel range or less) will improve signal-to-noise ratio (SNR) in assessing confidence that a hand sanitation event has occurred. This is because although the resampling to a coarser resolution inherently entails loss of information, the operation of resampling to a coarser resolution also operates to smooth the imaging data as higher spatial frequency components are suppressed or removed. This higher spatial frequency content is typically dominated by noise, rather than being useful signal content. When looking at a model that determines whether a hand sanitation event occurs or does not in a video frame, it might be expected that utilizing a larger and higher resolution image for the model would lead to higher classification accuracies. However, it is recognized herein that this is not the case. The reason a smaller sanitation zone is more accurate and computationally efficient for recognizing a hand sanitation event can be understood as follows. When applying a CNN or other ML classifier to attempt to learn to detect an outcome (here a hand sanitation event), the classifier is trained to find patterns in the pixels that correlate with the outcome. In other words, it attempts to group the pattern in the picture of pixels by the label that was given. The CNN or other ML classifier does not know what specific patterns it associates with the outcome, or whether it is correct. Therefore, when the classifier is looking at finding patterns in the associated outcome or action it is desirable to give the classifier an image with clean patterns and low noise to the greatest extent possible. In addition to accuracy, computing on a wash station zone with a smaller set of pixels (and hence less information) leads to greater computational efficiency. To achieve this goal the system leverages two main steps (i) cropping the image to the wash station zone, and (ii) smoothing that preserves image gradients. These steps are preferably optimized to keep the optimal amount of pertinent information while cutting incidental patterns. It should be noted that the cropping may be omitted if the computational capacity of the electronic processor 24 is sufficient to process the frames without cropping at sufficient speed (e.g., within the frame rate of the video, i.e. each frame should be processed before the next frame is acquired and presented for processing). Additionally or alternatively, the smoothing may optionally be omitted.

The region around a wash station is typically busy with nurses and doctors rushing from room to room and ward to ward. When looking at a full video frame (e.g., for 720p video a frame has a height of 720 pixels and a width of 1,280 pixels) there are many different patterns from the various moving persons. If the CNN 60 receive full frames (e.g. 720×1280 pixel frames of 720p video) then detecting a difference between a full frame capturing a hand sanitation event versus a full frame that does not capture a hand sanitation event, the CNN 60 will see many patterns and correlations that are not necessarily relevant to the difference outcome. Incorrect correlation of a non-relevant pattern to a relevant outcome pattern can lead to bias and inaccuracies. By cropping the image processed by the CNN 60 to the area around the hand sanitation station, the CNN is fed the essential information and patterns relevant to detecting a hand sanitation event. However, if taken too far this can also lead to an inaccurate classifier. When the size of the crop is reduced, relevant patterns may be removed. The relevance of these removed patterns may not be apparent to the designer of the classifier, but would be useful input for improving the accuracy of the classifier. By way of a specific example, only looking at the sanitation zone may cut out a window or other reflective surface that the designer might not recognize to be relevant for detecting a hand sanitation event, but that might in fact improve the classifier accuracy. Hence, the size of the wash station zone 40 should preferably include all important relevant patterns, while reducing or eliminating non-relevant patterns. In addition to accuracy, computing on less pixels increases overall system speed.

In addition to design of the pixel dimensions of the wash station zone 40, another way to improve classifier accuracy is to provide the classifier 60 with an image having clean patterns and low noise to the extent possible. This can be achieved by smoothing without losing gradients containing relevant information in the image. Smoothing is a computer vision mechanism based on kernel mathematics to reduce or eliminate high-frequency, outlier heavy aspects of an image. An approximating function should be used that captures important patterns in the data, while leaving out noise or other fine-scale structures that might otherwise be incorrectly matched to patterns indicative of a hand sanitation event. The sample array values of the image are modified so the individual points are reduced and the points that are lower than the adjacent points are increased leading to a smoother signal and less variation. Therefore, a sample series of data points are taken from the image, and a filter or kernel of various sizes and aggregation methods is applied and repeatedly iterated through the image to output a smoothed image. By way of a non-limiting illustrative example, a linear filter may be used for smoothing, which determines the output pixels by a simple weighted value from the surrounding pixels of various size. This is represented, for example, by the below Equation (1):

$$O(r, g, b) = \sum_{r,g,b} f(r+k, g+l, b+k)h(k, l, h) \quad (1)$$

As shown in Equation (1), the output pixels O(r,g,b) in red, green, and blue, respectively, is equal to the sum of the kernel h(k, l, h) multiplied by the weighted sum of the input pixels f(r+k, g+l, b+k), as expressed in Equation (1). The kernel is, in this example, a matrix with a fixed size 15×15, which looks at the 15 pixels to consider in Equation (1). Therefore, the kernel is just a coefficient to the filter or the "window size" and the filter is a sliding "window" that goes across portions of the image to output different sized and averaged array tensors or "smoother image." In other words, this image transformation is applied to each pixel in the image to achieve a different state. The goal of this operation is to smooth the image, which can reduce the noise. However, the smoothing can also smooth away the edges and important information and patterns that are relevant for detecting a hand sanitation event. Hence, over-smoothing can lead to an inaccurate classifier and reduced real time accuracy. To address this, the smoothing operation may optionally incorporate an Image Gradient to smooth away noise while retaining the relevant patterns. This problem is solved by looking at the rate of change in the pixels to determine important edges and features. By grouping pixels that are close to one another in value and close to one another in spatial location and leveraging Laplacian, Robers or Prewitt operations these "edges" can be found. In other words, these operations are designed to automatically limit the smoothing at "edges" in images by highly polarized pixel values. Therefore, the gradients build on the smoothing operation to be defined as Bilateral filtering, as expressed, for example, by Equation (2):

$$I^{filtered}(x) = \sum_{x1 \in \Omega} I(x1)Fr(\|I(x1) - I(x)\|)Gs(\|x1 - x\|) \quad (2)$$

As shown in Equation (2) above, I is the original input image, x is the coordinates of the current pixel, Q is the "isolator window" centered in x, Fr is the range kernel for smoothing differences in intensities, and Gs is the spatial kernel for smoothing difference in coordinates. So by utilizing the rate of change of the two different smoothing operations "un-important" pixels can be smoothed while bringing out "important" pixels. This leads to a pixel window that is optimized for the most relevant patterns to show. This allows a greater chance for the classifier training to attach correct correlation to outcomes, while still allowing for the unpredictable correlations to be present. Therefore these operations affect the training and system side positively. First off, training on higher accurate data and less physical information increases training accuracy, iteration speed and overall computation efficiency. On the inference side cropping, smoothing and gradients allow for less pixels to be consumed which allows for real-time monitoring to be possible, while increasing inference accuracy. The described bilateral filtering is merely an illustrative example, and other types of filtering could be employed to facilitate locating the sanitation zone, for example edge-detection filtering to enhance the strongest edges in the image.

The same down-sampling operations that encompass the smoothing and image gradients can be up-sampled. This means that for a blurry or smaller pixel window the image processing can attempt to make a sharper "better" image. This is done by finding the inverse of the functions set forth above. Therefore, the sanitation zone could be up-sampled or down-sampled to be any pixel range, suitably chosen to optimize accuracy of the classifier by avoiding losing too much relevant information or adding too much noise.

As noted previously, the wash station zone 40 should coincide with the spatial region within which the hand sanitation is expected to be performed by a person using the hand sanitation station 10. During installation, the video camera 20 is positioned to capture the sanitation zone, and the installer delineates the area of a frame that depicts the wash station zone 40; accordingly, the extraction of the image of the wash station zone at operation 102 merely entails extracting that pre-delineated area of the frame. The image may optionally entail further preprocessing to condition the image of the wash station zone for input to the CNN 60. For example, in the illustrative embodiment at an operation 103 the extracted image of the wash station zone is converted to RGB (i.e. red-green-blue) 3×3 channel arrays (tensor). More generally, the image of the wash station zone extracted from the frame 100 may be converted to a tensor of channel arrays wherein each channel array represents a color channel of the image of the wash station zone. The color channels may be RGB color channels as in the illustrative example, or may be color channels of another color space such as LAB, YCrCb, HSV, or so forth. In other embodiments, it is contemplated to replace (or augment) the RGB, YCrCb, HSV, or other color video feed with depth information. A depth camera could be used or a regular camera could be used utilizing a depth map function. The depth of a pixel could be found using disparity=x−x=Bf/Z. Utilizing this, the depth of all pixels in an image can be derived. However, it is expected that employing depth information would increase the computational load and may lead to an image with less distinctive sanitation attributes. Other types of imaging, such as thermal imaging could also be used. In an operation 104, the CNN 60 is applied to the extracted (and optionally preprocessed) image of the wash station zone to generate a confidence value 106 indicative of likelihood that the image of the wash station zone depicts a hand sanitation event. In this regard, it should be noted that the training images of the wash station zone 40 or of a standard wash station zone used to (pre-)train the CNN (or other ML classifier) 60 should have been processed using the same extraction/preprocessing 102. For example, if the preprocessing 102 includes converting to RGB 3×3 channel arrays prior to input to the CNN 60 at operation 104, then the training images should also have been converted to RGB 3×3 channel arrays prior to use in training the CNN.

At an operations 107, 108, the confidence 106 is assessed to determine whether the frame depicts an occurrence of a hand sanitation event. For example, if the confidence 106 is higher than some threshold (e.g., an x-value), then it is determined that a hand sanitation event occurred 64, and the process of FIG. 3 stops. In another approach (illustrated), a multiple-criteria decision making or analysis (MCDM or MCDA) 107 is employed to assess whether the confidence 106 to determine whether the frame depicts an occurrence of a hand sanitation event. MCDM is a process of evaluating multiple conflicting criteria with different weights for decision making. In the instant case, the MCDM 107 can be an aggregation method, which in one approach involves reading the confidence metrics from the model for a certain value and make a decision based on that. In other words, the binary decision of whether an event occurred is made based on the events that occurred and their weights. Many aggregation-based MCDM approaches are known, including Geometric Median (GM), Non-Conventional Matching (NCM), The LogStructed Merge-Tree (LSM-Tree), Singular Value Decomposition Method (SVDM), Ordered Weighted Averaging (OWA), Dynamic AHP (Analytic Hierarchy Process), ELETRE TRI, Technique for Order of Preference by Similarity to Ideal Solution that is based on Bayesian vector networks, which is based on the distance of each alternative from the ideal solution (TOPSIS) with interval data, Fuzzy Analytic Hierarchy Process (FAHP) which uses pairwise comparison metrics to than aggregate through fuzzy numbers, Fuzzy MCDM, which is based on trapezoidal fuzzy numbers through a TOOPSIS degree method, Multi-Attribute Utility (MAU), and variants of these. As an illustrative example, an approach employing the OWA aggregation operator is described. This OWA gives the technique for directly aggregating "uncertain" information with "uncertain" weights. The uncertainty regards what action is being committed (hand sanitation event or no hand sanitation event) and uncertainty weights indicate how confident the model is about the information. An OWA is defined, for example, as in Equation (3):

$$\phi(a) = \phi(a_1, \ldots, a_n) = \sum_{i=1}^{n} \omega_i a_{\sigma(i)} \quad (3)$$

In the above Equation (3), $\phi$ is a mapping specified as $\phi$: $\mathbb{R}^n \to \mathbb{R}$ which has weights defined as $w=(\omega_1, \ldots, \omega_n)^T$ where the weights or confidence readings, $\omega_1, \ldots, \omega_n$, are between 0-1 and the sum of the weights is equal to one, i.e. $w_i \epsilon [0,1]$ for all i=1, . . . , n, and $\Sigma_{i=1}^{n} w_i = 1$. Using Equation (3), an aggregation method is formed that helps connect the linguistic outputs (here hand sanitation and no hand sanitation) with unsure values and weights. This is merely one illustrative aggregation method, and other simpler or more complex aggregation methods can be utilized, or other approaches as already mentioned.

On the other hand, if the frame is not sufficient to determine that a hand sanitation event occurred (i.e., if the confidence does not meet the threshold x-value), then in an operation 110 the result is aggregated with confidence values for earlier frames. At an operation 112, it is determined whether the person is still in the sanitation zone (that is, it is determined whether the occupancy time interval is continuing or has ended). If the person is still in the sanitation zone then a next frame 114 of the video (which may be the immediately next frame in the video stream providing a 30 Hz time resolution at 30 fps, or the fifth next frame providing a 6 Hz resolution at 30 fps, or so forth) is obtained and processed by the operations 102, 104, 108, 110 as described. This continues until the occupancy time interval ends, at which time the operation 112 will determine the person is no longer in the sanitation zone. At this point, in an operation 116 the aggregation of confidences from the operation 110 is examined to determine whether it can be concluded that no hand sanitation event occurred over the occupancy time interval. This can employ various statistical approaches. In one approach, the largest confidence from any of the processed frames is compared with a threshold y-value, and if it is below this threshold y-value then it is determined that no hand sanitation event occurred 66, and the process of FIG. 3 stops. On the other hand, if it is determined at the operation 110 that the largest confidence is above the threshold y-value (but below the threshold x-value since otherwise processing would have stopped at the operation 108 due to a positive determination 64), then the result is ambiguous and the resulting hand hygiene compliance status is deemed to be indeterminate. This may in some embodiments be treated as a noncompliance so as to provide the final reminder to the person before he or she passes through the door 18; or, the indeterminate result may be treated differently from either a positive determination of compliance or positive determination of noncompliance, e.g. an indeterminate result may cause no annunciated output. In the optional statistics database 80, the indeterminate result is preferably recorded as indeterminate, so that the resulting compliance report identifies the fraction of times the compliance enforcement device was unable to make a positive determination.

In the operations 108, 116, the respective thresholds x-value and y-value may be suitably optimized during the training of the CNN (or other ML classifier) 60, e.g. being an additional two parameters to be optimized in addition to the activation weights and/or other parameters of the CNN 60.

The illustrative embodiment of the operation 62 presented with reference to FIG. 2 is merely an illustrative example, and numerous variants are contemplated. Other types of artificial neural networks (ANNs) can be employed in place of the illustrative CNN 60, or even more generally other types of classifiers may be employed in place of the CNN 60, such as a support vector machine (SVM) classifier. In general, a machine learning (ML) classifier (including CNN, ANN, SVM, and other ML classifiers) may be used. Moreover, other types of analyses may be employed. For example, FIG. 3 illustrates an optional color classifier analysis operation 118, which may be employed in addition to, or in place of, the CNN analysis 104. In this case, it is assumed that the hand sanitation fluid dispensed at the sanitation station 10 has a distinctive color. Hence, in the color classifier analysis operation 118, it is determined whether that color is (sufficiently) present in the image of the wash station zone, and a confidence is computed (or adjusted) on the basis of the color metric output by the color classifier analysis operation 118. Other types of visual cues detectable in the acquired video frame may be the basis for the classifier analysis, such as reflectivity, brightness (or, equivalently, dimness), texture metrics, or so forth.

The illustrative embodiments describe detection of a hand sanitation event via analysis of extracted images of the wash station. In the case of a "gown and glove" procedure such as is employed in a C-DIFF protocol, it is additionally contemplated to employ similar analysis of an image of a gowning zone (e.g., proximate to a closet containing gowns to be put on during the gowning part of the C-DIFF protocol) to detect a gowning event, so as to monitor compliance with both the gowning and gloving aspects of the C-DIFF or similar gown-and-glove procedure. In this case, the CNN or other ML classifier is trained using training videos of persons gowning (positive examples) or failing to gown (negative examples) in a manner analogous to the training described for the illustrative CNN 60. The electronic processor 24 is used to determine whether a gowning event occurs based on images of a gowning zone extracted from the real time video, and the compliance status (variant of 64 or 66 of FIG. 2) is further based on the determination of whether a gowning event occurs. More specifically, a ML classifier is applied to the images of the gowning zone extracted from successive frames of the real time video to generate per-frame gowning event confidence values, and the determination is made of whether a gowning event occurs based on the per-frame gowning event confidence values for the successive frames. The ML classifier for generating the per-frame gowning event confidence values is pre-trained using training images of the gowning zone or a standard gowning zone that depict a gowning event and training images of the gowning zone or the standard gowning zone that do not depict a gowning event.

The illustrative examples employ a single video camera 20 as shown in FIG. 1. However, it is contemplated to employ more than one video camera. For example, one video camera may be provided which is arranged to capture a wide FOV encompassing the area 54 and the sanitation zone; while, a second video camera is arranged with a narrower FOV to capture the smaller wash station zone 40. This may allow for more accurate determination of whether a hand sanitation event occurs due to more optimal placement of the second video camera respective to the wash station zone 40. In another contemplated variant, a single video camera may be positioned to capture the wash station zone 40, but the occupancy time interval may be determined by non-camera-based sensor(s) such as motion sensors or depth sensors as previously discussed. In this case, the occupancy detection instructions 30 are suitably replaced by instructions processing the output of the non-camera-based sensor(s) to determine the occupancy time interval.

The preferred embodiments have been illustrated and described. Obviously, modifications and alterations will occur to others upon reading and understanding the preceding detailed description. It is intended that the invention be construed as including all such modifications and alterations insofar as they come within the scope of the appended claims or the equivalents thereof.

Aspects of the Present Disclosure

The following aspects of the disclosure are exemplary only and not intended to limit the scope of the disclosure.

1. A hand hygiene compliance enforcement device comprising: at least one video camera; at least one annunciator; an electronic processor; and a non-transitory storage medium storing instructions that are readable and executable by the electronic processor to process real time video acquired by the at least one video camera in real time, the instructions including: occupancy detection instructions readable and executable by the electronic processor to analyze the real time video to determine an occupancy time interval over which a sanitation zone imaged by the real time video is occupied; and sanitation detection instructions readable and executable by the electronic processor to determine whether a hand sanitation event occurs based on images of a wash station zone extracted from the real time video acquired during the occupancy time period and to control the at least one annunciator to annunciate a hand hygiene compliance status based on the determination of whether a hand sanitation event occurs.

2. The hand hygiene compliance enforcement device of aspect 1, wherein the sanitation detection instructions are readable and executable by the electronic processor to determine whether a hand sanitation event occurs by operations including: for each frame of successive frames of the real time video acquired during the occupancy time period, applying a machine learning (ML) classifier to the image of the wash station zone extracted from the frame to generate a confidence value indicative of likelihood that the image of the wash station zone depicts a hand sanitation event; and determining whether a hand sanitation event occurs in the wash station zone based on the confidence values for the successive frames, wherein the ML classifier is pre-trained to generate the confidence value using training images of the wash station zone or a standard wash station zone that depict a hand sanitation event and training images of the wash station zone or the standard wash station zone that do not depict a hand sanitation event.

3. The hand hygiene compliance enforcement device of aspect 2, wherein the applying of the ML classifier includes: converting the image of the wash station zone extracted from the frame to a tensor of channel arrays wherein each channel array represents a color channel of the image of the wash station zone; and applying the ML classifier to the tensor of channel arrays.

4. The hand hygiene compliance enforcement device of any one of aspects 1-3, wherein the images of the wash station zone extracted from the real time video acquired during the occupancy time period have pixel dimensions L×W where L is 100 pixels or less and W is 100 pixels or less.

5. The hand hygiene compliance enforcement device of aspect 4, wherein the extracting of the images of the wash station zone from the real time video acquired during the occupancy time period includes pixel resampling, the pixel dimensions L×W being after the pixel resampling.

6. The hand hygiene compliance enforcement device of any one of aspects 1-5, wherein the sanitation detection instructions are readable and executable by the electronic processor to determine whether a hand sanitation event occurs in the wash station zone by operations including: detecting a color of a hand sanitation fluid in the images of the wash station zone extracted from the real time video acquired during the occupancy time period.

7. The hand hygiene compliance enforcement device of any one of aspects 1-6, wherein the occupancy detection instructions are readable and executable by the electronic processor to analyze the real time video to determine the occupancy time interval by operations including at least one of: for successive frames of the real time video, extracting an image of the sanitation zone from the frame and comparing the extracted image of the sanitation zone with a reference image of the sanitation zone to detect whether the extracted image of the sanitation zone indicates occupation of the sanitation zone; and/or for successive frames of the real time video, extracting an image of the sanitation zone from the frame and comparing the images of the sanitation zone extracted from the successive frames of the real time video to detect frame-to-frame changes that indicate occupation of the sanitation zone.

8. The hand hygiene compliance enforcement device of any one of aspects 1-7, wherein the at least one annunciator comprises a noncompliance light and the sanitation detection instructions are readable and executable by the electronic processor to annunciate the hand hygiene compliance status by at least one of: a) controlling the noncompliance light to illuminate starting at the beginning of the occupancy time interval and ending at the earlier of (i) a stop time respective to the end of the occupancy time interval or (ii) a time when it is determined that a hand sanitation event occurs; b) controlling the noncompliance light to illuminate starting at the end of the occupancy time interval if it is determined that no hand sanitation event occurred during the occupancy time interval.

9. The hand hygiene compliance enforcement device of aspect 8, wherein the at least one annunciator further comprises a compliance light and the sanitation detection instructions are readable and executable by the electronic processor to further annunciate the hand hygiene compliance status by at least one of: a) controlling the compliance light to illuminate starting at a time in the occupancy time interval when it is determined that a hand sanitation event occurs; b) controlling the compliance light to illuminate starting at the end of the occupancy time interval if it is determined that a hand sanitation event occurred during the occupancy time interval.

10. The hand hygiene compliance enforcement device of any one of aspects 8-9, wherein the noncompliance light is illuminated by a flashing illumination.

11. The hand hygiene compliance enforcement device of any one of aspects 1-10, wherein the at least one annunciator includes at least one of: an at least one light and/or an audio speaker and/or a display.

12. The hand hygiene compliance enforcement device of any one of aspects 1-11, wherein the instructions stored on the non-transitory storage medium that are readable and executable by the electronic processor to process the real time video acquired by the at least one video camera do not include instructions readable and executable by the electronic processor to identify a person in the sanitation zone.

13. The hand hygiene compliance enforcement device of aspect 12, wherein the instructions further include: reporting instructions readable and executable by the electronic processor to accumulate statistics for a plurality of successive occupancy time periods on corresponding determinations of whether a hand sanitation event occurs and generate a compliance report on the accumulated statistics.

14. The hand hygiene compliance enforcement device of any one of aspects 1-13, wherein the instructions further include: reporting instructions readable and executable by the electronic processor to identify a person in the sanitation zone during the occupancy time period using a radio frequency identification (RFID) reader that detects RFID badges or facial recognition applied to the real time video; and accumulate statistics for a plurality of successive occupancy time periods on corresponding determinations of whether a hand sanitation event occurs and generate a compliance report on the accumulated statistics including identification of persons identified in the sanitation zone using the facial recognition during occupancy time periods for which the corresponding determination of whether a hand sanitation event occurs is that no hand sanitation event occurred.

15. The hand hygiene compliance enforcement device of any one of aspects 1-14, wherein the at least one video camera consists of a single video camera and the wash station zone is contained in the sanitation zone imaged by the real time video.

16. A hand sanitation station including: a hand sanitation station including at least a sanitation fluid dispenser; and a hand hygiene compliance enforcement device as set forth in any one of aspects 1-15, wherein the at least one video camera is arranged such that at least a portion of the hand sanitation station coincides with the wash station zone in the real time video acquired by the at least one video camera.

17. A non-transitory storage medium storing instructions that are readable and executable by an electronic processor operatively connected with at least one video camera and at least one annunciator to process real time video acquired by the at least one video camera in real time to perform a hand hygiene compliance enforcement method comprising: analyzing the real time video to determine an occupancy time interval over which a sanitation zone imaged by the real time video is occupied; determining whether a hand sanitation event occurs based on images of a wash station zone extracted from the real time video acquired during the occupancy time period; and controlling the at least one annunciator to annunciate a hand hygiene compliance status based on the determination of whether a hand sanitation event occurs.

18. The non-transitory storage medium of aspect 17, wherein the determining of whether a hand sanitation event occurs comprises: applying a Convolutional Neural Network (CNN) to the images of the wash station zone extracted from successive frames of the real time video acquired during the occupancy time period to generate per-frame confidence values; and determining whether a hand sanitation event occurs based on the per-frame confidence values for the successive frames, wherein the CNN is pre-trained to generate confidence values indicating confidence that input images depict a hand sanitation event using training images of the wash station zone or a standard wash station zone that depict a hand sanitation event and training images of the wash station zone or the standard wash station zone that do not depict a hand sanitation event.

19. The non-transitory storage medium of aspect 18, wherein the applying of the CNN includes: converting the image of the wash station zone extracted from the frame to a tensor of channel arrays wherein each channel array represents a principal color channel of the image of the wash station zone; and applying the CNN to the tensor of channel arrays.

20. The non-transitory storage medium of any one of aspects 17-19, wherein the images of the wash station zone extracted from the real time video acquired during the occupancy time period have pixel dimensions L×W where L is 100 pixels or less and W is 100 pixels or less.

21. The non-transitory storage medium of aspect 20, wherein the extracting of the images of the wash station zone from the real time video acquired during the occupancy time period includes pixel resampling, the pixel dimensions L×W being after the pixel resampling.

22. The non-transitory storage medium of any one of aspects 16-21, wherein the hand hygiene compliance enforcement method further comprises: accumulating statistics for a plurality of successive occupancy time periods on corresponding determinations of whether a hand sanitation event occurs; and generating a compliance report on the accumulated statistics.

23. A hand hygiene compliance enforcement method comprising: using at least one video camera, acquiring real time video of a field of view that includes a sanitation station having a wash station zone; using an electronic processor, determining whether a hand sanitation event occurs based on images of the wash station zone extracted from the real time video; and using an annunciator, annunciating a compliance status based on the determination of whether a hand sanitation event occurs.

24. The hand hygiene compliance enforcement method of aspect 23, wherein the determining of whether a hand sanitation event occurs comprises: applying a machine learning (ML) classifier to the images of the wash station zone extracted from successive frames of the real time video to generate per-frame confidence values; and determining whether a hand sanitation event occurs based on the per-frame confidence values for the successive frames, wherein the ML classifier is pre-trained using training images of the wash station zone or a standard wash station zone that depict a hand sanitation event and training images of the wash station zone or the standard wash station zone that do not depict a hand sanitation event.

25. The hand hygiene compliance enforcement method of aspect 24, wherein the applying of the ML classifier includes: converting the image of the wash station zone extracted from the frame to a tensor of channel arrays wherein each channel array represents a principal color channel of the image of the wash station zone; and applying the ML classifier to the tensor of channel arrays.

26. The hand hygiene compliance enforcement method of any one of aspects 23-25 further comprising: analyzing the real time video to determine an occupancy time interval over which a sanitation zone imaged by the real time video is occupied; wherein the determining of whether a hand sanitation event occurs is based on images of the wash station zone extracted from only the real time video acquired during the occupancy time interval.

27. The hand hygiene compliance enforcement method of any one of aspects 23-26 further comprising: using the electronic processor, determining whether a gowning event occurs based on images of a gowning zone extracted from the real time video, wherein the compliance status is further based on the determination of whether a gowning event occurs.

28. The hand hygiene compliance enforcement method of aspect 27, wherein the determining of whether a gowning event occurs comprises: applying a machine learning (ML) classifier to the images of the gowning zone extracted from successive frames of the real time video to generate per-frame gowning event confidence values; and determining whether a gowning event occurs based on the per-frame gowning event confidence values for the successive frames, wherein the ML classifier for generating the per-frame gowning event confidence values is pre-trained using training images of the gowning zone or a standard gowning zone that depict a gowning event and training images of the gowning zone or the standard gowning zone that do not depict a gowning event.

Additional Aspects of the Present Disclosure

The following additional aspects of the disclosure are exemplary only and not intended to limit the scope of the disclosure.

1. A hand hygiene compliance enforcement device comprising: at least one video camera; at least one annunciator; an electronic processor; and a non-transitory storage medium storing instructions that are readable and executable by the electronic processor, wherein the instructions, when executed by the electronic processor, cause the electronic processor to: process real time video acquired by the at least one video camera in real time, analyze, by execution of occupancy detection instructions, the real time video to determine an occupancy time interval over which a sanitation zone imaged by the real time video is occupied, determine, by execution of sanitation detection instructions, whether a hand sanitation event occurs based on images of a wash station zone as extracted from the real time video acquired during the occupancy time interval, and control the at least one annunciator to annunciate a hand hygiene compliance status based on the determination of whether a hand sanitation event occurs.

2. The hand hygiene compliance enforcement device of aspect 1, wherein the electronic processor is configured to execute the sanitation detection instructions to cause the electronic processor to: apply, for each respective frame of successive frames of the real time video acquired during the occupancy time interval, a machine learning (ML) classifier to one or more images of the wash station zone as extracted from the respective frame to generate a confidence value indicative of likelihood that the one or more images of the wash station zone depicts a hand sanitation event, and determine whether a hand sanitation event occurs in the wash station zone based on the confidence values for the successive frames, wherein the ML classifier is pre-trained to generate the confidence value using (1) training images of the wash station zone or a standard wash station zone that depicts a hand sanitation event, and (2) training images of the wash station zone or the standard wash station zone that do not depict a hand sanitation event.

3. The hand hygiene compliance enforcement device of aspect 2, wherein application of the ML classifier comprises: converting an image of the wash station zone as extracted from a frame of the successive frames to a tensor of channel arrays, wherein each channel array represents a color channel of the image of the wash station zone; and applying the ML classifier to the tensor of channel arrays.

4. The hand hygiene compliance enforcement device as in any one of aspects 1-3, wherein the images of the wash station zone, as extracted from the real time video acquired during the occupancy time interval, have pixel dimensions length (L) by width (W) where L is 100 pixels or less and W is 100 pixels or less, wherein extraction of the images of the wash station zone from the real time video acquired during the occupancy time interval comprises pixel resampling, the pixel dimensions L by W being determined after the pixel resampling.

5. The hand hygiene compliance enforcement device as in any one of aspects 1-4, wherein the electronic processor is configured to execute the sanitation detection instructions to cause the electronic processor to: determine whether a hand sanitation event occurs in the wash station zone by detecting a color of a hand sanitation fluid in the images of the wash station zone as extracted from the real time video acquired during the occupancy time interval.

6. The hand hygiene compliance enforcement device as in any one of aspects 1-5, wherein the electronic processor is configured to execute the occupancy detection instructions to cause the electronic processor to perform at least one of: a) extracting, for one or more successive frames of the real time video, an extracted image of the sanitation zone from a frame of the one or more successive frames, and comparing the extracted image of the sanitation zone with a reference image of the sanitation zone to detect whether the extracted image of the sanitation zone indicates occupation of the sanitation zone; or b) extracting, for two or more successive frames of the real time video, an extracted image of the sanitation zone from a respective frame of the two or more successive frames, and comparing a first image of the sanitation zone as extracted from a first respective frame of the two or more successive frames with a second image of the sanitation zone as extracted from a second respective frame of the two or more successive frames to detect frame-to-frame changes that indicate occupation of the sanitation zone.

7. The hand hygiene compliance enforcement device as in any one of aspects 1-6, wherein the at least one annunciator comprises a noncompliance light, and wherein the electronic processor is configured to execute the sanitation detection instructions to cause the electronic processor to perform at least one of: a) controlling the noncompliance light to illuminate starting at a beginning of the occupancy time interval and ending at the earlier of (i) a stop time respective to an end of the occupancy time interval, or (ii) a time determined when a hand sanitation event occurs; or b) controlling the noncompliance light to illuminate starting at an end of the occupancy time interval upon a determination that no hand sanitation event occurred during the occupancy time interval.

8. The hand hygiene compliance enforcement device of aspect 7, wherein the at least one annunciator further comprises a compliance light, and wherein the electronic processor is configured to execute the sanitation detection instructions to cause the electronic processor to perform at least one of: a) controlling the compliance light to illuminate starting at a time in the occupancy time interval upon a determination that a hand sanitation event occurs; b) controlling the compliance light to illuminate starting at an end of the occupancy time interval upon a determination that a hand sanitation event occurred during the occupancy time interval.

9. The hand hygiene compliance enforcement device of aspect 7, wherein the noncompliance light is illuminated by a flashing illumination.

10. The hand hygiene compliance enforcement device as in any one of aspects 1-9, wherein the at least one annunciator comprises at least one of: a light; an audio speaker; a display; or, a touchscreen display.

11. The hand hygiene compliance enforcement device as in any one of aspects 1-10, wherein the instructions are configured to lack or filter identification of a person in the sanitation zone.

12. The hand hygiene compliance enforcement device of aspect 11, wherein the instructions comprise reporting instructions readable and executable by the electronic processor, the reporting instructions that when executed by the electronic processor, cause the electronic processor to: accumulate data statistics for a plurality of successive occupancy time intervals on corresponding determinations of whether a hand sanitation event occurs and generate a compliance report on the data statistics.

13. The hand hygiene compliance enforcement device as in any one of aspects 1-12, wherein the instructions comprise reporting instructions readable and executable by the electronic processor, the reporting instructions that when executed by the electronic processor, cause the electronic processor to: identify a person in the sanitation zone during the occupancy time interval using (i) a radio frequency identification (RFID) reader that detects RFID badges, or (ii) facial recognition applied to the real time video; accumulate data statistics for a plurality of successive occupancy time intervals on corresponding determinations of whether a hand sanitation event occurs; and generate a compliance report based on the data statistics including identification of one or more persons identified in the sanitation zone during occupancy time intervals for which the corresponding determination of whether a hand sanitation event occurs is that no hand sanitation event occurred.

14. The hand hygiene compliance enforcement device as in any one of aspects 1-13, wherein the at least one video camera consists of a single video camera and the wash station zone is contained in the sanitation zone imaged by the real time video.

15. The hand hygiene compliance enforcement device as in any one of aspects 1-14 further comprising: a hand sanitation station including at least a sanitation fluid dispenser, wherein the at least one video camera is positioned such that at least a portion of the hand sanitation station coincides with the wash station zone in the real time video acquired by the at least one video camera.

16. A non-transitory storage medium storing instructions for performing a hand hygiene compliance enforcement, instructions being readable and executable by an electronic processor, wherein the instructions, when executed by the electronic processor, cause the electronic processor to: receive real time video acquired by at least one video camera in real time; analyze the real time video to determine an occupancy time interval over which a sanitation zone imaged by the real time video is occupied; determine whether a hand sanitation event occurs based on images of a wash station zone as extracted from the real time video acquired during the occupancy time interval; and control at least one annunciator to annunciate a hand hygiene compliance status based on the determination of whether a hand sanitation event occurs.

17. The non-transitory storage medium of aspect 16, wherein determination of whether the hand sanitation event occurs comprises: applying a convolutional neural network (CNN) to the images of the wash station zone as extracted from successive frames of the real time video acquired during the occupancy time interval to generate per-frame confidence values; and determining whether the hand sanitation event occurs based on the per-frame confidence values, wherein the CNN is pre-trained to generate confidence values indicating confidence that input images depict a hand sanitation event using training images of the wash station zone or a standard wash station zone that depict a hand sanitation event and training images of the wash station zone or the standard wash station zone that do not depict a hand sanitation event.

18. The non-transitory storage medium of aspect 17 wherein application of the CNN comprises: converting the image of the wash station zone as extracted from a frame of the successive frames to a tensor of channel arrays wherein each channel array represents a color channel of the image of the wash station zone; and applying the CNN to the tensor of channel arrays.

19. The non-transitory storage medium as in any one of aspects 1-17, wherein the instructions, when executed by the electronic processor, further cause the electronic processor to: accumulate data statistics for a plurality of successive occupancy time intervals on corresponding determinations of whether a hand sanitation event occurs; and generate a compliance report based on the data statistics.

20. A hand hygiene compliance enforcement method comprising: acquiring, via a at least one video camera, real time video of a field of view that includes a sanitation station having a wash station zone; determining, via an electronic processor, whether a hand sanitation event occurs based on images of the wash station zone as extracted from the real time video; and annunciating, via an annunciator, a compliance status based on the determination of whether a hand sanitation event occurs.

21. The hand hygiene compliance enforcement method of aspect 20, wherein determination of whether a hand sanitation event occurs comprises: applying a machine learning (ML) classifier to the images of the wash station zone as extracted from successive frames of the real time video to generate per-frame confidence values; and determining whether a hand sanitation event occurs based on the per-frame confidence values for the successive frames, wherein the ML classifier is pre-trained using training images of the wash station zone or a standard wash station zone that depict a hand sanitation event and training images of the wash station zone or the standard wash station zone that do not depict a hand sanitation event.

22. The hand hygiene compliance enforcement method of aspect 21, wherein application of the ML classifier comprises: converting an image of the wash station zone as extracted from the frame of the successive frames to a tensor of channel arrays, wherein each channel array represents a color channel of the image of the wash station zone; and applying the ML classifier to the tensor of channel arrays.

23. The hand hygiene compliance enforcement method as in any one of aspects 1-22 further comprising analyzing the real time video to determine an occupancy time interval over which a sanitation zone imaged by the real time video is occupied, wherein the determination of whether a hand sanitation event occurs is based on images of the wash station zone as extracted from only the real time video acquired during the occupancy time interval.

24. The hand hygiene compliance enforcement method as in any one of aspects 1-23 further comprising determining, with the electronic processor, whether a gowning event occurs based on images of a gowning zone as extracted from the real time video, wherein the compliance status is further based on the determination of whether a gowning event occurs.

25. The hand hygiene compliance enforcement method of aspect 24, wherein determination of whether the gowning event occurs comprises: applying a machine learning (ML) classifier to the images of the gowning zone as extracted from successive frames of the real time video to generate per-frame gowning event confidence values; and determining whether the gowning event occurs based on the per-frame gowning event confidence values for the successive frames, wherein the ML classifier for generating the per-frame gowning event confidence values is pre-trained using training images of the gowning zone or a standard gowning zone that depict a gowning event and training images of the gowning zone or the standard gowning zone that do not depict a gowning event.

26. A hand hygiene compliance enforcement device comprising: at least one non-camera-based sensor; at least one annunciator; an electronic processor; and a non-transitory storage medium storing instructions that are readable and executable by the electronic processor, wherein the instructions, when executed by the electronic processor, cause the electronic processor to: process real time data output of the non-camera-based sensor in real time, analyze, by execution of occupancy detection instructions, the data output to determine an occupancy time interval over which a sanitation zone determined by the data output is occupied, determine, by execution of sanitation detection instructions, whether a hand sanitation event occurs based on the data output corresponding to a wash station zone, the data output acquired during the occupancy time interval, and control the at least one annunciator to annunciate a hand hygiene compliance status based on the hand sanitation event.

27. The hand hygiene compliance enforcement device of aspect 26, wherein the electronic processor is configured to execute the sanitation detection instructions to cause the electronic processor to: apply, for each series of data output of the non-camera-based sensor as acquired during the occupancy time interval, a machine learning (ML) classifier to sensor data corresponding to the wash station zone, to generate a confidence value indicative of likelihood that the sensor data of the wash station zone corresponds a hand sanitation event, and determine whether a hand sanitation event occurs in the wash station zone based on the confidence values for the successive frames, wherein the ML classifier is pre-trained to generate the confidence value using training sensor data of the wash station zone or a standard wash station zone that defines a hand sanitation event and sensor data of the wash station zone or the standard wash station zone that do not correspond to a hand sanitation event.

28. The hand hygiene compliance enforcement device of aspect 27, wherein application of the ML classifier comprises: converting sensor data of the wash station zone to a tensor of channel arrays, wherein each channel array emulates a color channel of an image of the wash station zone; and applying the ML classifier to the tensor of channel arrays.

29. The hand hygiene compliance enforcement device of aspect 1 further comprising an information sharing application comprising an information sharing interface, the information sharing interface configured to display sanitation or hygiene compliance data or information.

30. The hand hygiene compliance enforcement device of aspect 1 further comprising a hand hygiene marketing platform comprising a marketing interface, the marketing interface configured to display advertisements to users in the sanitation zone or a marketing zone.

Additional Considerations

Although the disclosure herein sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location, while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other embodiments, the one or more processors or processor-implemented modules may be distributed across a number of geographic locations.

This detailed description is to be construed as exemplary only and does not describe every possible embodiment, as describing every possible embodiment would be impractical, if not impossible. A person of ordinary skill in the art may implement numerous alternate embodiments, using either current technology or technology developed after the filing date of this application.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

What is claimed is:

1. A hand hygiene compliance enforcement device comprising:
    at least one video camera;
    at least one annunciator; an electronic processor; and
    a non-transitory storage medium storing instructions that are readable and executable by the electronic processor, wherein the instructions, when executed by the electronic processor, cause the electronic processor to:
    process real time video acquired by the at least one video camera in real time,
    analyze, by execution of occupancy detection instructions, the real time video to determine an occupancy time interval over which a sanitation zone imaged by the real time video is occupied,
    determine, by execution of sanitation detection instructions, whether a hand sanitation event occurs based on images of a wash station zone as extracted from the real time video acquired during the occupancy time interval,
    control the at least one annunciator to annunciate a hand hygiene compliance status based on the determination of whether a hand sanitation event occurs, and
    applying a convolutional neural network (CNN) to the images of the wash station zone as extracted from successive frames of the real time video acquired during the occupancy time interval to generate per-frame confidence values: and
    determining whether the hand sanitation event occurs based on the per-frame confidence values,
    wherein the CNN is pre-trained to generate confidence values indicating confidence that input images depict a hand sanitation event using training images of the wash station zone or a standard wash station zone that depict a hand sanitation event and training images of the wash station zone or the standard wash station zone that do not depict a hand sanitation event.

2. The hand hygiene compliance enforcement device of claim 1, wherein the electronic processor is configured to execute the sanitation detection instructions to cause the electronic processor to:

apply, for each respective frame of successive frames of the real time video acquired during the occupancy time interval, a machine learning (ML) classifier to one or more images of the wash station zone as extracted from the respective frame to generate a confidence value indicative of likelihood that the one or more images of the wash station zone depicts a hand sanitation event, and determine whether a hand sanitation event occurs in the wash station zone based on the confidence values for the successive frames, wherein the ML classifier is pre-trained to generate the confidence value using (1) training images of the wash station zone or a standard wash station zone that depicts a hand sanitation event, and (2) training images of the wash station zone or the standard wash station zone that do not depict a hand sanitation event.

3. The hand hygiene compliance enforcement device of claim 2, wherein application of the ML classifier comprises: converting an image of the wash station zone as extracted from a frame of the successive frames to a tensor of channel arrays, wherein each channel array represents a color channel of the image of the wash station zone; and
applying the ML classifier to the tensor of channel arrays.

4. The hand hygiene compliance enforcement device of claim 1, wherein the images of the wash station zone, as extracted from the real time video acquired during the occupancy time interval, have pixel dimensions length (L) by width (W) where L is 100 pixels or less and W is 100 pixels or less, and
wherein extraction of the images of the wash station zone from the real time video acquired during the occupancy time interval comprises pixel resampling, the pixel dimensions L by W being determined after the pixel resampling.

5. The hand hygiene compliance enforcement device of claim 1, wherein the electronic processor is configured to execute the occupancy detection instructions to cause the electronic processor to perform at least one of:
  a) extracting, for one or more successive frames of the real time video, an extracted image of the sanitation zone from a frame of the one or more successive frames, and comparing the extracted image of the sanitation zone with a reference image of the sanitation zone to detect whether the extracted image of the sanitation zone indicates occupation of the sanitation zone; or
  b) extracting, for two or more successive frames of the real time video, an extracted image of the sanitation zone from a respective frame of the two or more successive frames, and comparing a first image of the sanitation zone as extracted from a first respective frame of the two or more successive frames with a second image of the sanitation zone as extracted from a second respective frame of the two or more successive frames to detect frame-to-frame changes that indicate occupation of the sanitation zone.

6. The hand hygiene compliance enforcement device of claim 1, wherein the at least one annunciator comprises a noncompliance light, and wherein the electronic processor is configured to execute the sanitation detection instructions to cause the electronic processor to perform at least one of:
  a) controlling the noncompliance light to illuminate starting at a beginning of the occupancy time interval and ending at the earlier of (i) a stop time respective to an end of the occupancy time interval, or (ii) a time determined when a hand sanitation event occurs; or
  b) controlling the noncompliance light to illuminate starting at an end of the occupancy time interval upon a determination that no hand sanitation event occurred during the occupancy time interval.

7. The hand hygiene compliance enforcement device of claim 6, wherein the at least one annunciator further comprises a compliance light, and wherein the electronic processor is configured to execute the sanitation detection instructions to cause the electronic processor to perform at least one of:
  a) controlling the compliance light to illuminate starting at a time in the occupancy time interval upon a determination that a hand sanitation event occurs;
  b) controlling the compliance light to illuminate starting at an end of the occupancy time interval upon a determination that a hand sanitation event occurred during the occupancy time interval.

8. The hand hygiene compliance enforcement device of claim 6, wherein the noncompliance light is illuminated by a flashing illumination.

9. The hand hygiene compliance enforcement device of claim 1, wherein the at least one annunciator comprises at least one of:
  a light;
  an audio speaker; a display; or
  a touchscreen display.

10. The hand hygiene compliance enforcement device of claim 1, wherein the instructions are configured to lack or filter identification of a person in the sanitation zone.

11. The hand hygiene compliance enforcement device of claim 10, wherein the instructions comprise reporting instructions readable and executable by the electronic processor, the reporting instructions that when executed by the electronic processor, cause the electronic processor to:
  accumulate data statistics for a plurality of successive occupancy time intervals on corresponding determinations of whether a hand sanitation event occurs and generate a compliance report on the data statistics.

12. The hand hygiene compliance enforcement device of claim 1, wherein the instructions comprise reporting instructions readable and executable by the electronic processor, the reporting instructions that when executed by the electronic processor, cause the electronic processor to:
  identify a person in the sanitation zone during the occupancy time interval using (i) a radio frequency identification (RFID) reader that detects RFID badges, or (ii) facial recognition applied to the real time video;
  accumulate data statistics for a plurality of successive occupancy time intervals on corresponding determinations of whether a hand sanitation event occurs; and
  generate a compliance report based on the data statistics including identification of one or more persons identified in the sanitation zone during occupancy time intervals for which the corresponding determination of whether a hand sanitation event occurs is that no hand sanitation event occurred.

13. The hand hygiene compliance enforcement device of claim 1, wherein the at least one video camera consists of a single video camera and the wash station zone is contained in the sanitation zone imaged by the real time video.

14. The hand hygiene compliance enforcement device of claim 1 further comprising:
a hand sanitation station including at least a sanitation fluid dispenser, wherein the at least one video camera is positioned such that at least a portion of the hand sanitation station coincides with the wash station zone in the real time video acquired by the at least one video camera.

15. A non-transitory storage medium storing instructions for performing a hand hygiene compliance enforcement, instructions being readable and executable by an electronic processor, wherein the instructions, when executed by the electronic processor, cause the electronic processor to:
  receive real time video acquired by at least one video camera in real time; analyze the real time video to determine an occupancy time interval over which a sanitation zone imaged by the real time video is occupied;
  determine whether a hand sanitation event occurs based on images of a wash station zone as extracted from the real time video acquired during the occupancy time interval;
  control at least one annunciator to annunciate a hand hygiene compliance status based on the determination of whether a hand sanitation event occurs,
  applying a convolutional neural network (CNN) to the images of the wash station zone as extracted from successive frames of the real time video acquired during the occupancy time interval to generate per-frame confidence values: and determining whether the hand sanitation event occurs based on the per-frame confidence values,
  wherein the CNN is pre-trained to generate confidence values indicating confidence that input images depict a hand sanitation event using training images of the wash station zone or a standard wash station zone that depict a hand sanitation event and training images of the wash station zone or the standard wash station zone that do not depict a hand sanitation event.

16. The non-transitory storage medium of claim 15 wherein application of the CNN comprises:
  converting the image of the wash station zone as extracted from a frame of the successive frames to a tensor of channel arrays wherein each channel array represents a color channel of the image of the wash station zone; and applying the CNN to the tensor of channel arrays.

17. The non-transitory storage medium of claim 15, wherein the instructions, when executed by the electronic processor, further cause the electronic processor to:
  accumulate data statistics for a plurality of successive occupancy time intervals on corresponding determinations of whether a hand sanitation event occurs; and
  generate a compliance report based on the data statistics.

18. A hand hygiene compliance enforcement method comprising:
  acquiring, via a at least one video camera, real time video of a field of view that includes a sanitation station having awash station zone;
  determining, via an electronic processor, whether a hand sanitation event occurs based on images of the wash station zone as extracted from the real time video; and
  annunciating, via an annunciator, a compliance status based on the determination of whether a hand sanitation event occurs; and
  wherein determining a hand sanitation event comprises:
  applying a convolutional neural network (CNN) to the images of the wash station zone as extracted from successive frames of the real time video acquired during the occupancy time interval to generate per-frame confidence values, and
  determining whether the hand sanitation event occurs based on the per-frame confidence values, wherein the CNN is pre-trained to generate confidence values indicating confidence that input images depict a hand sanitation event using training images of the wash station zone or a standard wash station zone that depict a hand sanitation event and training images of the wash station zone or the standard wash station zone that do not depict a hand sanitation event.

19. The hand hygiene compliance enforcement method of claim 18, wherein determination of whether a hand sanitation event occurs comprises:
  applying a machine learning (ML) classifier to the images of the wash station zone as extracted from successive frames of the real time video to generate per-frame confidence values; and
  determining whether a hand sanitation event occurs based on the per-frame confidence values for the successive frames, wherein the ML classifier is pre-trained using training images of the wash station zone or a standard wash station zone that depict a hand sanitation event and training images of the wash station zone or the standard wash station zone that do not depict a hand sanitation event.

20. The hand hygiene compliance enforcement method of claim 19, wherein application of the ML classifier comprises: converting an image of the wash station zone as extracted from the frame of the successive frames to a tensor of channel arrays, wherein each channel array represents a color channel of the image of the wash station zone; and applying the ML classifier to the tensor of channel arrays.

21. The hand hygiene compliance enforcement method of claim 18 further comprising analyzing the real time video to determine an occupancy time interval over which a sanitation zone imaged by the real time video is occupied, wherein the determination of whether a hand sanitation event occurs is based on images of the wash station zone as extracted from only the real time video acquired during the occupancy time interval.

22. The hand hygiene compliance enforcement method of claim 18 further comprising determining, with the electronic processor, whether a gowning event occurs based on images of a gowning zone as extracted from the real time video, wherein the compliance status is further based on the determination of whether a gowning event occurs.

23. The hand hygiene compliance enforcement method of claim 22, wherein determination of whether the gowning event occurs comprises:
  applying a machine learning (ML) classifier to the images of the gowning zone as extracted from successive frames of the real time video to generate per-frame gowning event confidence values; and
  determining whether the gowning event occurs based on the per-frame gowning event confidence values for the successive frames, wherein the ML classifier for generating the per-frame gowning event confidence values is pre-trained using training images of the gowning zone or a standard gowning zone that depict a gowning event and training images of the gowning zone or the standard gowning zone that do not depict a gowning event.

24. A hand hygiene compliance enforcement device comprising:
  at least one non-camera-based sensor;
  at least one annunciator;
  an electronic processor; and
  a non-transitory storage medium storing instructions that are readable and executable by the electronic processor, wherein the instructions, when executed by the electronic processor, cause the electronic processor to:
  process real time data output of the non-camera-based sensor in real time, analyze, by execution of occupancy detection instructions, the data output to determine an occupancy time interval over which a sanitation zone determined by the data output is occupied, determine, by execution of sanitation detection instructions, whether a hand sanitation event occurs based on the data output corresponding to a wash station zone, the data output acquired during the occupancy time interval, control the at least one annunciator to annunciate a hand hygiene compliance status based on the hand sanitation event, and applying a convolutional neural network (CNN) to the images of the wash station zone as extracted from successive frames of the real time video acquired during the occupancy time interval to generate per-frame confidence values: and determining whether the hand sanitation event occurs based on the per-frame confidence values, wherein the CNN is pre-trained to generate confidence values indicating confidence that input images depict a hand sanitation event using training images of the wash station zone or a standard wash station zone that depict a hand sanitation event and training images of the wash station zone or the standard wash station zone that do not depict a hand sanitation event.

25. The hand hygiene compliance enforcement device of claim 24, wherein the electronic processor is configured to execute the sanitation detection instructions to cause the electronic processor to:

apply, for each series of data output of the non-camera-based sensor as acquired during the occupancy time interval, a machine learning (ML) classifier to sensor data corresponding to the wash station zone, to generate a confidence value indicative of likelihood that the sensor data of the wash station zone corresponds a hand sanitation event, and determine whether a hand sanitation event occurs in the wash station zone based on the confidence values for the successive frames, wherein the ML classifier is pre-trained to generate the confidence value using training sensor data of the wash station zone or a standard wash station zone that defines a hand sanitation event and sensor data of the wash station zone or the standard wash station zone that do not correspond to a hand sanitation event.

26. The hand hygiene compliance enforcement device of claim 25, wherein application of the ML classifier comprises:

converting sensor data of the wash station zone to a tensor of channel arrays, wherein each channel array emulates a color channel of an image of the wash station zone; and applying the ML classifier to the tensor of channel arrays.

27. The hand hygiene compliance enforcement device of claim 1 further comprising an information sharing application comprising an information sharing interface, the information sharing interface configured to display sanitation or hygiene compliance data or information.

28. The hand hygiene compliance enforcement device of claim 1 further comprising a hand hygiene marketing platform comprising a marketing interface, the marketing interface configured to display advertisements to users in the sanitation zone or a marketing zone.

29. The hand hygiene compliance enforcement device of claim 1, wherein the electronic processor is configured to execute the sanitation detection instructions to cause the electronic processor to:

determine whether a hand sanitation event occurs in the wash station zone by detecting a color of a hand sanitation fluid in the images of the wash station zone as extracted from the real time video acquired during the occupancy time interval.

\* \* \* \* \*

UNITED STATES PATENT AND TRADEMARK OFFICE
CERTIFICATE OF CORRECTION

PATENT NO. : 11,017,655 B2  
APPLICATION NO. : 17/067172  
DATED : May 25, 2021  
INVENTOR(S) : John Caleb Harman et al.

Page 1 of 1

It is certified that error appears in the above-identified patent and that said Letters Patent is hereby corrected as shown below:

In the Claims

At Column 36, Line 54, "values:" should be -- values; --.

At Column 39, Line 15, "occurs," should be -- occurs; --.

At Column 41, Line 17, "values:" should be -- values; --.

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*